United States Patent
Timm et al.

(10) Patent No.: US 7,713,287 B2
(45) Date of Patent: May 11, 2010

(54) DYNAMIC SPINE STABILIZER

(75) Inventors: Jens Peter Timm, West Haven, CT (US); Manohar M. Panjabi, North Haven, CT (US)

(73) Assignees: Applied Spine Technologies, Inc., Rocky Hill, CT (US); Yale University, New Haven, CT (US)

(*) Notice: Subject to any disclaimer, the term of this patent is extended or adjusted under 35 U.S.C. 154(b) by 324 days.

(21) Appl. No.: 11/132,538

(22) Filed: May 19, 2005

(65) Prior Publication Data

US 2005/0245930 A1 Nov. 3, 2005

Related U.S. Application Data

(63) Continuation-in-part of application No. 10/835,109, filed on Apr. 30, 2004, now Pat. No. 7,029,475.

(60) Provisional application No. 60/506,724, filed on Sep. 30, 2003, provisional application No. 60/467,414, filed on May 2, 2003.

(51) Int. Cl.
*A61B 17/70* (2006.01)
(52) U.S. Cl. .................. 606/257; 606/259; 606/261
(58) Field of Classification Search ............. 606/60, 606/61, 250, 256, 257, 259, 261; 128/898; 623/17.11–17.16
See application file for complete search history.

(56) References Cited

U.S. PATENT DOCUMENTS

| | | | |
|---|---|---|---|
| 2,733,596 A | 2/1956 | Painter | |
| 3,807,394 A | 4/1974 | Attenborough | 606/60 |
| 4,328,960 A * | 5/1982 | Handke et al. | 267/226 |

(Continued)

FOREIGN PATENT DOCUMENTS

AU    744241    7/1999

(Continued)

OTHER PUBLICATIONS

Panjabi, The Stabilizing System of the Spine, Part I. Function, Dysfunction, Adaptation, and Enhancement, Journal of Spinal Disorders, 1992, vol. 5, No. 4, pp. 383-389.

(Continued)

*Primary Examiner*—Pedro Philogene
(74) *Attorney, Agent, or Firm*—McCarter & English, LLP

(57) ABSTRACT

A dynamic spine stabilization device is provided that includes at least one force imparting member, e.g., a spring. The force imparting member is adapted to deliver a force of between about 150 lb/inch and 450 lbs/inch, and restrict the relative travel distance between said first and second pedicles to a distance of between about 1.5 mm and 5 mm. The spinal stabilization devices also have a minimal impact on the location of the center of rotation for the spinal segment being treated. By providing resistance in the noted range and restricting the travel distance to the noted range, it has been found that the stabilization device provides a desired level of stabilization, as reflected by range of motion values that closely approximate pre-injury range of motion levels. In addition, the resistance levels are not so high as to alter the location of the center of rotation of the treated spinal segment from its normal anatomical location to levels previously obtained, thereby permitting substantially unimpeded angular motion despite the posterior presence of a stabilization device.

16 Claims, 12 Drawing Sheets

U.S. PATENT DOCUMENTS

| | | | |
|---|---|---|---|
| 4,352,514 A | 10/1982 | Orima | |
| 4,558,852 A | 12/1985 | Steiner et al. | |
| 4,650,167 A | 3/1987 | Steiner et al. | |
| 4,743,260 A | 5/1988 | Burton | |
| 4,759,769 A | 7/1988 | Hedman et al. | |
| 5,034,011 A | 7/1991 | Howland | |
| 5,092,867 A | 3/1992 | Harms et al. | |
| 5,174,551 A | 12/1992 | Mintgen | |
| 5,180,393 A | 1/1993 | Commarmond | |
| 5,291,901 A | 3/1994 | Graf | |
| 5,329,933 A | 7/1994 | Graf | |
| 5,375,823 A * | 12/1994 | Navas | 623/17.15 |
| 5,415,661 A | 5/1995 | Holmes | |
| 5,423,816 A | 6/1995 | Lin | |
| 5,480,401 A * | 1/1996 | Navas | 606/61 |
| 5,501,684 A | 3/1996 | Schlapfer et al. | |
| 5,505,118 A | 4/1996 | Arnesen et al. | |
| 5,540,688 A | 7/1996 | Navas | |
| 5,562,737 A | 10/1996 | Graf | |
| 5,653,680 A | 8/1997 | Cruz | |
| 5,672,175 A | 9/1997 | Martin | |
| 5,733,284 A | 3/1998 | Martin | 606/61 |
| RE36,221 E | 6/1999 | Breard et al. | |
| 5,961,516 A | 10/1999 | Graf | |
| 6,162,223 A | 12/2000 | Orsak et al. | |
| 6,176,860 B1 | 1/2001 | Howard | |
| 6,241,730 B1 | 6/2001 | Alby | |
| 6,267,764 B1 | 7/2001 | Elberg | |
| 6,293,949 B1 | 9/2001 | Justis et al. | |
| 6,375,681 B1 | 4/2002 | Truscott | |
| 6,402,750 B1 | 6/2002 | Atkinson et al. | |
| 6,419,706 B1 | 7/2002 | Graf | |
| 6,440,169 B1 | 8/2002 | Elberg et al. | |
| 6,508,818 B2 | 1/2003 | Steiner et al. | |
| 6,554,831 B1 | 4/2003 | Rivard et al. | |
| 6,645,207 B2 | 11/2003 | Dixon et al. | |
| 6,761,719 B2 | 7/2004 | Justis et al. | |
| 6,796,984 B2 | 9/2004 | Soubeiran | 606/86 |
| 6,835,205 B2 * | 12/2004 | Atkinson et al. | 623/17.11 |
| 6,986,771 B2 | 1/2006 | Paul et al. | 606/61 |
| 6,989,011 B2 | 1/2006 | Paul et al. | 606/61 |
| 7,029,475 B2 * | 4/2006 | Panjabi | 606/61 |
| 7,329,258 B2 | 2/2008 | Studer | |
| 2002/0095154 A1 | 7/2002 | Atkinson et al. | |
| 2002/0133155 A1 | 9/2002 | Ferree | 606/61 |
| 2002/0151978 A1 | 10/2002 | Zacouto et al. | |
| 2003/0055427 A1 | 3/2003 | Fraf | |
| 2003/0171749 A1 | 9/2003 | Le Couedic et al. | |
| 2003/0220642 A1 | 11/2003 | Freudiger | |
| 2003/0220643 A1 * | 11/2003 | Ferree | 606/61 |
| 2004/0049189 A1 | 3/2004 | Le Couedic et al. | |
| 2004/0049190 A1 | 3/2004 | Biedermann et al. | |
| 2004/0082954 A1 | 4/2004 | Teitelbaum et al. | |
| 2004/0143264 A1 | 7/2004 | McAfee | |
| 2004/0147928 A1 | 7/2004 | Landry et al. | |
| 2004/0167523 A1 | 8/2004 | Jackson | |
| 2004/0236329 A1 | 11/2004 | Panjabi | |
| 2005/0049708 A1 | 3/2005 | Atkinson et al. | 623/17.16 |
| 2005/0065514 A1 | 3/2005 | Studer | |
| 2005/0085815 A1 | 4/2005 | Harms et al. | 606/59 |
| 2005/0154390 A1 | 7/2005 | Biedermann et al. | 606/59 |
| 2005/0165396 A1 | 7/2005 | Fortin et al. | 606/61 |
| 2005/0203519 A1 | 9/2005 | Harms et al. | 606/61 |
| 2005/0216017 A1 | 9/2005 | Fielding et al. | |
| 2005/0261682 A1 | 11/2005 | Ferree | 606/61 |
| 2005/0261685 A1 | 11/2005 | Fortin et al. | 606/61 |
| 2005/0277922 A1 | 12/2005 | Trieu et al. | 606/72 |
| 2005/0288672 A1 | 12/2005 | Ferree | 606/61 |
| 2006/0009767 A1 | 1/2006 | Kiester | 606/61 |
| 2006/0036240 A1 | 2/2006 | Colleran et al. | 606/61 |
| 2006/0041259 A1 | 2/2006 | Paul et al. | 606/61 |
| 2006/0064090 A1 | 3/2006 | Park | 606/61 |
| 2006/0079898 A1 | 4/2006 | Ainsworth et al. | 623/17.11 |
| 2006/0084994 A1 | 4/2006 | Atkinson et al. | 623/17.16 |
| 2006/0129147 A1 | 6/2006 | Biedermann et al. | 606/61 |
| 2006/0142758 A1 | 6/2006 | Petit | 606/61 |
| 2006/0142760 A1 | 6/2006 | McDonnell | 606/61 |
| 2006/0155279 A1 | 7/2006 | Ogilvie | 606/105 |
| 2006/0189983 A1 | 8/2006 | Fallin et al. | 606/61 |
| 2006/0189984 A1 | 8/2006 | Fallin et al. | 606/61 |
| 2006/0212033 A1 | 9/2006 | Rothman et al. | 606/61 |
| 2006/0229612 A1 | 10/2006 | Rothman et al. | 606/61 |
| 2006/0247637 A1 | 11/2006 | Colleran et al. | 606/61 |
| 2006/0264940 A1 | 11/2006 | Hartmann | 123/458 |
| 2006/0293657 A1 | 12/2006 | Martmann | 606/61 |
| 2007/0016190 A1 | 1/2007 | Martinez et al. | 606/61 |

FOREIGN PATENT DOCUMENTS

| | | | |
|---|---|---|---|
| CA | 2135838 | 5/1995 | |
| CA | 2213058 | 2/1998 | |
| EP | 0516567 | 12/1992 | |
| EP | 0534874 | 3/1993 | |
| EP | 0576379 | 12/1993 | |
| EP | 0611554 | 8/1994 | |
| EP | 0821917 | 2/1998 | |
| EP | 1039855 | 6/2004 | |
| FR | 2676911 | 12/1992 | |
| FR | 2681520 | 3/1993 | |
| FR | 2692468 | 12/1993 | |
| FR | 2694182 | 2/1994 | |
| FR | 2701650 | 8/1994 | |
| FR | 2701651 | 8/1994 | |
| FR | 2751864 | 2/1998 | |
| FR | 2772594 | 6/1999 | |
| FR | 2775891 | 9/1999 | |
| FR | 2794362 | 12/2000 | |
| FR | 2799949 | 4/2001 | |
| FR | 2801782 | 6/2001 | |
| FR | 2803188 | 7/2001 | |
| FR | 2809304 | 11/2001 | |
| FR | 2810873 | 1/2002 | |
| FR | 2812535 | 2/2002 | |
| GB | 2382304 | 5/2003 | |
| JP | 6-285100 | 10/1994 | |
| JP | 7-289562 | 11/1995 | |
| JP | 10-71157 | 3/1998 | |
| JP | 10-277070 | 10/1998 | |
| WO | 99/32054 | 7/1999 | |
| WO | 01/39678 | 6/2001 | |
| WO | 01/45576 | 6/2001 | |
| WO | 01/49192 | 7/2001 | |
| WO | WO 01/49192 * | 7/2001 | 606/61 |
| WO | 02/00124 | 1/2002 | |
| WO | 02/102259 | 12/2002 | |
| WO | 03/047442 | 6/2003 | |
| WO | WO 03/047442 * | 6/2003 | 606/250 |

OTHER PUBLICATIONS

Panjabi, The Stabilizing System of the Spine Part II. Neutral Zone and Instability Hypothesis, Journal of Spinal Disorders, 1992, vol. 5, No. 4, pp. 390-397.
PCT International Search Report dated Feb. 22, 2006.
PCT International Search Report dated Aug. 31, 2007.
European Search Report dated Mar. 8, 2007.
European Patent Summons to Oral Proceedings dated Jun. 11, 2008.

* cited by examiner

DSS in Tension

DSS in Tension

Free-body diagram

DYNAMIC SPINE STABILIZER

CROSS REFERENCE TO RELATED APPLICATIONS

This application claims the benefit of two provisional patent applications: U.S. Ser. No. 60/506,724, entitled "DYNAMIC SPINE STABILIZER", filed Sep. 30, 2003, and U.S. Ser. No. 60/467,414, entitled "DYNAMIC SPINE STABILIZER", filed May 2, 2003. This application is also a continuation-in-part application that claims the benefit of a, non-provisional patent application: U.S. Ser. No. 10/835,109, entitled "DYNAMIC SPINE STABILIZER", filed Apr. 30, 2004 now U.S. Pat. No. 7,029,475. The contents of each of the foregoing applications is incorporated herein by reference.

BACKGROUND OF THE INVENTION

1. Field of the Invention

The invention relates to a method and apparatus for spinal stabilization. More particularly, the invention relates to a spinal stabilization device, system and/or apparatus (and associated methods) that deliver desirable levels of stabilization to a spine while maintaining or preserving physiologically desirable levels and/or degrees of spinal motion.

2. Description of the Prior Art

Low back pain is one of the most expensive diseases afflicting industrialized societies. With the exception of the common cold, it accounts for more doctor visits than any other ailment. The spectrum of low back pain is wide, ranging from periods of intense disabling pain which resolve, to varying degrees of chronic pain. The conservative treatments available for lower back pain include: cold packs, physical therapy, narcotics, steroids and chiropractic maneuvers. Once a patient has exhausted all conservative therapy, the surgical options range from micro discectomy, a relatively minor procedure to relieve pressure on the nerve root and spinal cord, to fusion, which takes away spinal motion at the level of pain.

Each year, over 200,000 patients undergo lumbar fusion surgery in the United States. While fusion is effective about seventy percent of the time, there are consequences even to these successful procedures, including a reduced range of motion and an increased load transfer to adjacent levels of the spine, which accelerates degeneration at those levels. Further, a significant number of back-pain patients, estimated to exceed seven million in the U.S., simply endure chronic low-back pain, rather than risk procedures that may not be appropriate or effective in alleviating their symptoms.

New treatment modalities, collectively called motion preservation devices, are currently being developed to address these limitations. Some promising therapies are in the form of nucleus, disc or facet replacements. Other motion preservation devices provide dynamic internal stabilization of the injured and/or degenerated spine, without removing any spinal tissues. A major goal of this concept is the stabilization of the spine to prevent pain while preserving near normal spinal function. The primary difference in the two types of motion preservation devices is that replacement devices are utilized with the goal of replacing degenerated anatomical structures which facilitates motion while dynamic internal stabilization devices are utilized with the goal of stabilizing and controlling abnormal spinal motion without removing any tissue.

Over ten years ago a hypothesis of low back pain was presented in which the spinal system was conceptualized as consisting of the spinal column (vertebrae, discs and ligaments), the muscles surrounding the spinal column, and a neuromuscular control unit which helps stabilize the spine during various activities of daily living. Panjabi M M. "The stabilizing system of the spine. Part I. Function, dysfunction, adaptation, and enhancement." J Spinal Disord 5 (4): 383-389, 1992a. A corollary of this hypothesis was that strong spinal muscles are needed when a spine is injured or degenerated. This was especially true while standing in neutral posture. Panjabi M M. "The stabilizing system of the spine. Part II. Neutral zone and instability hypothesis." J Spinal Disord 5 (4): 390-397, 1992b. In other words, a low-back patient needs to have sufficient well-coordinated muscle forces, strengthening and training the muscles where necessary, so they provide maximum protection while standing in neutral posture.

Dynamic stabilization (non-fusion) devices need certain functionality in order to assist the compromised (injured or degenerated with diminished mechanical integrity) spine of a back patient. Specifically, the devices must provide mechanical assistance to the compromised spine, especially in the neutral zone where it is needed most. The "neutral zone" refers to a region of low spinal stiffness or the toe-region of the Moment-Rotation curve of the spinal segment (see FIG. 1). Panjabi M M, Goel V K, Takata K. 1981 Volvo Award in Biomechanics. "Physiological Strains in Lumbar Spinal Ligaments, an in vitro Biomechanical Study." Spine 7 (3): 192-203, 1982. The neutral zone is commonly defined as the central part of the range of motion around the neutral posture where the soft tissues of the spine and the facet joints provide least resistance to spinal motion. This concept is nicely visualized on a load-displacement or moment-rotation curve of an intact and injured spine as shown in FIG. 1. Notice that the curves are non-linear; that is, the spine mechanical properties change with the amount of angulations and/or rotation. If we consider curves on the positive and negative sides to represent spinal behavior in flexion and extension respectively, then the slope of the curve at each point represents spinal stiffness. As seen in FIG. 1, the neutral zone is the low stiffness region of the range of motion.

Experiments have shown that after an injury of the spinal column or due to degeneration, neutral zones, as well as ranges of motion, increase (see FIG. 1). However, the neutral zone increases to a greater extent than does the range of motion, when described as a percentage of the corresponding intact values. This implies that the neutral zone is a better measure of spinal injury and instability than the range of motion. Clinical studies have also found that the range of motion increase does not correlate well with low back pain. Therefore, the unstable spine needs to be stabilized especially in the neutral zone. Dynamic internal stabilization devices must be flexible so as to move with the spine, thus allowing the disc, the facet joints, and the ligaments normal physiological motion and loads necessary for maintaining their nutritional well-being. The devices must also accommodate the different physical characteristics of individual patients and anatomies to achieve a desired posture for each individual patient. Indeed, while providing spinal stabilization, it is highly desirable to permit substantially unrestricted angular motion for the spine.

With the foregoing in mind, those skilled in the art will understand that a need exists for a spinal stabilization device, system and/or apparatus which overcome the shortcomings of prior art devices. The present invention provides an advantageous device, system, apparatus and associated methods for spinal stabilization that deliver desirable levels and/or degrees of stabilization while maintaining and/or preserving physiologically desirable levels and/or degrees of spinal motion.

SUMMARY OF THE INVENTION

It is, therefore, an object of the present invention to provide a method for spinal stabilization that provides desirable levels of spinal stabilization while simultaneously permitting substantially unrestricted angular motion of the spine. The advantageous method of the present disclosure is achieved by securing a dynamic stabilizer to vertebrae of a spine and providing mechanical assistance in the form of resistance to a region of the spine to which the dynamic stabilizer is attached. In an exemplary embodiment of the present disclosure, the resistance is applied such that greater mechanical assistance is provided while the spine is around its neutral zone and lesser mechanical assistance is provided while the spine bends beyond its neutral zone.

According to further exemplary embodiments of the present invention, the disclosed spinal stabilization method involves providing a spinal stabilization device that delivers a predetermined level of resistance, while accommodating a predetermined travel distance (i.e., linear travel) between adjacent pedicles. To achieve the advantageous clinical results disclosed herein, the spinal stabilization device for use in the disclosed method is adapted to provide a predetermined level of resistance in the range of about 150 lbs/inch to about 450 lbs/inch. In addition, the spinal stabilization device for use in the disclosed method is adapted to permit a predetermined travel distance of about 1.5 mm to about 5 mm.

The present invention also provides an advantageous spinal stabilization device, system and/or apparatus that provides a predetermined level of resistance while simultaneously accommodating a predetermined travel distance (i.e., linear travel ($\Delta x$) between adjacent pedicles). In exemplary embodiments of the present disclosure, the disclosed dynamic stabilization device, system or apparatus is adapted for posterior placement and is adapted to provide a predetermined level of resistance in the range of about 150 to about 450 lbs/inch, and preferably between about 200 and about 400 lbs/inch, and to permit a predetermined travel distance of about 1.5 mm and about 5 mm, and preferably between about 2 mm and about 4 mm.

According to exemplary embodiments of the present disclosure, the dynamic stabilization device, system or apparatus moves under the control of spinal motion, providing increased mechanical support within a central zone corresponding substantially to a neutral zone of an injured spine. Exemplary dynamic stabilization devices include a support assembly and a resistance assembly associated with the support assembly. The resistance assembly generates resistance, applying greater resistance to movement during movement within the central zone and lower resistance to movement beyond the central zone.

Other objects and advantages of the present invention will become apparent from the following detailed description when viewed in conjunction with the accompanying drawings, which set forth certain embodiments of the invention.

BRIEF DESCRIPTION OF THE DRAWINGS

To assist those of ordinary skill in the art in making and using the disclosed spinal stabilization devices, systems and apparatus (and the associated methods), reference is made to the accompanying figures, wherein.

DESCRIPTION OF THE PREFERRED EMBODIMENTS

Exemplary embodiments of spinal stabilization devices, systems and apparatus (and associated methods) of the present invention are disclosed herein. It should be understood, however, that the disclosed embodiments are merely exemplary of the invention, which may be embodied in various forms. Therefore, the details disclosed herein are not to be interpreted as limiting, but rather as exemplary teachings that permit persons skilled in the art to make and/or use the disclosed devices, systems and apparatus (and associated methods).

With reference to FIGS. 2, 3a-c and 4, a method and apparatus are disclosed for spinal stabilization. In accordance with an exemplary embodiment of the present invention, the spinal stabilization method is achieved by securing an internal dynamic spinal stabilization device 10 between adjacent vertebrae 12, 14 and thereby providing mechanical assistance in the form of elastic resistance to the region of the spine to which the dynamic spinal stabilization device 10 is attached. The elastic resistance is applied as a function of displacement, such that greater mechanical assistance is provided while the spine is in its neutral zone and lesser mechanical assistance is provided while the spine bends beyond its neutral zone. Although the term "elastic resistance" is used throughout the body of the present specification, other forms of resistance may be employed without departing from the spirit or scope of the present invention.

Figure 2:
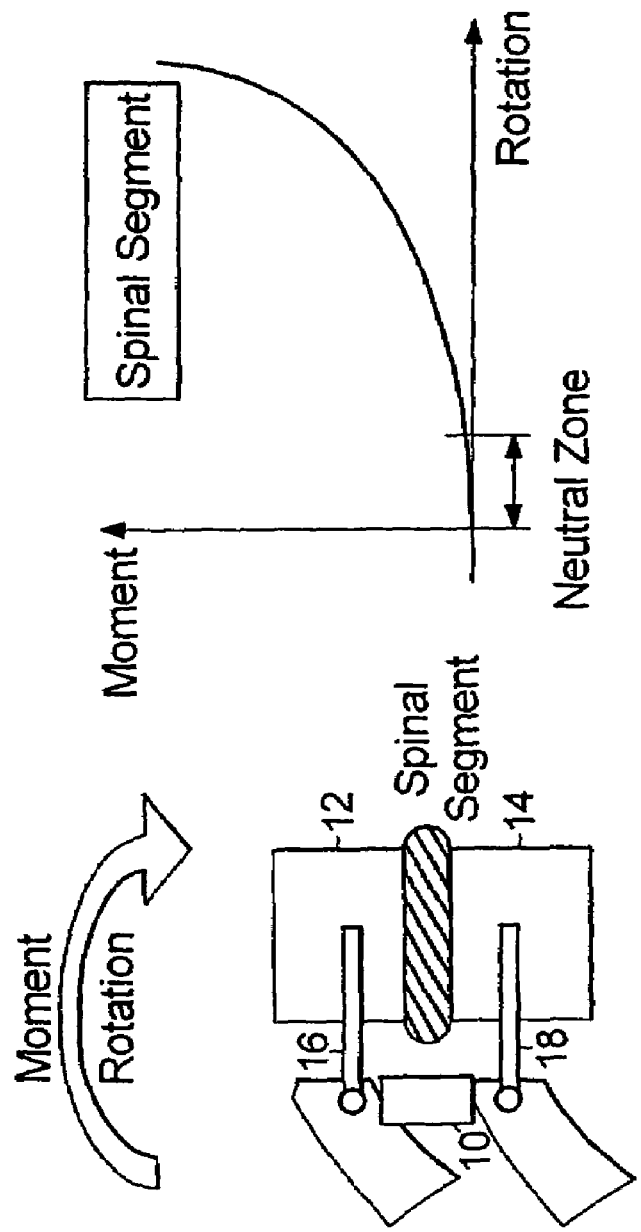
FIG. 2 is a schematic representation of a spinal segment in conjunction with a Moment-Rotation curve for a spinal segment, showing low spinal stiffness within the neutral zone.

As those skilled in the art will certainly appreciate, and as mentioned above, the "neutral zone" is understood to refer to a region of low spinal stiffness or the toe-region of the Moment-Rotation curve of the spinal segment (see FIG. 2). That is, the neutral zone may be considered to refer to a region of laxity around the neutral resting position of a spinal segment where there is minimal resistance to inter-vertebral motion. The range of the neutral zone is considered to be of major significance in determining spinal stability. Panjabi, M M. "The stabilizing system of the spine. Part II. Neutral zone and instability hypothesis." J Spinal Disorders 1992; 5(4): 390-397.

In fact, Dr. Panjabi has previously described the load displacement curve associated with spinal stability through the use of a "ball in a bowl" analogy. According to this analogy, the shape of the bowl indicates spinal stability. A deeper bowl represents a more stable spine, while a more shallow bowl represents a less stable spine. Dr. Panjabi previously hypothesized that for someone without spinal injury, there is a normal neutral zone (that part of the range of motion where there is minimal resistance to inter-vertebral motion) with a normal range of motion and, in turn, no spinal pain. In this instance, the bowl is not too deep nor too shallow. However, when an injury occurs to an anatomical structure, the neutral zone of the spinal column increases and the ball moves freely over a larger distance. By this analogy, the bowl would be more shallow and the ball less stable and, consequently, pain results from this enlarged neutral zone.

In general, pedicle screws 16, 18 are used to attach the dynamic spine stabilization device 10 to the vertebrae 12, 14 of the spine using well-tolerated and familiar surgical procedures known to those skilled in the art. In accordance with a preferred embodiment, and as those skilled in the art will certainly appreciate, a pair of opposed stabilizers are commonly used to balance the loads applied to the spine (see FIG. 3c). The dynamic spine stabilization device 10 assists the compromised (injured and/or degenerated) spine of a back pain patient, and helps her/him perform daily activities. The dynamic spine stabilization device 10 does so by providing controlled resistance to spinal motion particularly around neutral posture in the region of neutral zone. As the spine bends forward (flexion) the stabilization device 10 is tensioned (see FIG. 3d) and when the spine bends backward (extension) the stabilization device 10 is compressed (see FIG. 3e).

The resistance to displacement provided by the dynamic spine stabilization device 10 is non-linear, being greatest in its central zone so as to correspond to the individual's neutral zone; that is, the central zone of the stabilization device 10 provides a high level of mechanical assistance in supporting the spine. As the individual moves beyond the neutral zone, the increase in resistance decreases to a more moderate level. As a result, the individual encounters greater resistance to movement (or greater incremental resistance) while moving within the neutral zone.

According to exemplary embodiments of the present disclosure, the central zone of the dynamic spine stabilization device 10, that is, the range of motion in which the spine stabilization device 10 provides the greatest resistance to movement, may be adjustable at the time of surgery to suit the neutral zone of each individual patient. Indeed, the resistance to movement provided by the dynamic spine stabilization device 10 may be adjustable pre-operatively and intra-operatively. This functionality may serve to help to tailor the mechanical properties of the dynamic spine stabilization device 10 to suit the compromised spine of the individual patient. The length of the dynamic spine stabilization 10 may also be adjustable intra-operatively, to suit individual patient anatomy and to achieve desired spinal posture. According to exemplary embodiments of the present disclosure, the dynamic spine stabilization device 10 can be re-adjusted post-operatively with a surgical procedure to adjust its central zone to accommodate a patient's altered needs.

In exemplary embodiments, ball joints 36, 38 link the dynamic spine stabilization device 10 with the pedicle screws 16, 18. The junction of the dynamic spine stabilization device 10 and pedicle screws 16, 18 in such embodiments is free and rotationally unconstrained. Therefore, first of all, the spine is allowed all physiological motions of bending and twisting and second, the dynamic spine stabilization device 10 and the pedicle screws 16, 18 are protected from harmful bending and torsional forces, or moments. While ball joints are disclosed in accordance with an exemplary embodiment of the present invention, other linking structures, particularly linking structures that facilitate freedom of relative motion between the stabilization device and the pedicle screws, may be utilized without departing from the spirit or scope of the present invention.

As there are ball joints 36, 38 at each end of the stabilization device 10, bending moments are generally not transferred from the spine to the stabilization device 10. Further, the forces imparted by the stabilization device 10 with respect to the pedicle screws (and therefore the spine) are generally those forces associated with stabilizing components and/or stabilizing assemblies/sub-assemblies associated with stabilization device 10. As described in greater detail below, in an exemplary embodiment of the present disclosure, such forces are supplied through the relative positioning, mounting and stiffness of springs 30, 32 which may be positioned within a housing associated with stabilization device 10. The forces imparted by the stabilization device are dependent upon and responsive to the tension and compression applied to the stabilization device 10 as determined by spinal motion. Irrespective of the large loads on the spine, such as when a person carries or lifts a heavy load, the loads impacting upon operation of stabilization device 10 are dependent on and the result of spinal motion, and not the result of spinal load. The stabilization device 10 is, therefore, uniquely able to assist/stabilize the spine without enduring the high loads of the spine, allowing a wide range of design options pursuant to the teachings of the present disclosure.

The loading of the pedicle screws 16, 18 in exemplary implementations of the disclosed stabilization device 10 is also quite different from that in prior art pedicle screw fixation systems. In general terms, the only load that pedicle screws 16, 18 see is the force from the stabilization device 10. The forces generated by the stabilization device 10 translate into pure axial force at the ball joint-pedicle screw interface. This mechanism/junction arrangement greatly reduces the bending moment placed onto the pedicle screws 16, 18 as compared to prior art pedicle screw fusion systems. Thus, in exemplary embodiments of the present disclosure, due to the ball joints 36, 38, the bending moment within the pedicle screws 16, 18 is essentially zero at the ball joints 36, 38, and it increases toward the tip of the pedicle screws 16, 18. The area of pedicle screw-bone interface (which can be a failure site in a typical prior art pedicle screw fixation device) is a less stressed site relative to prior art implementations, and is therefore not likely to fail. In sum, the pedicle screws 16, 18, when used in conjunction with spinal stabilization devices according to the present invention, carry significantly less load and are placed under significantly less stress than typical pedicle screws.

Figure 1:
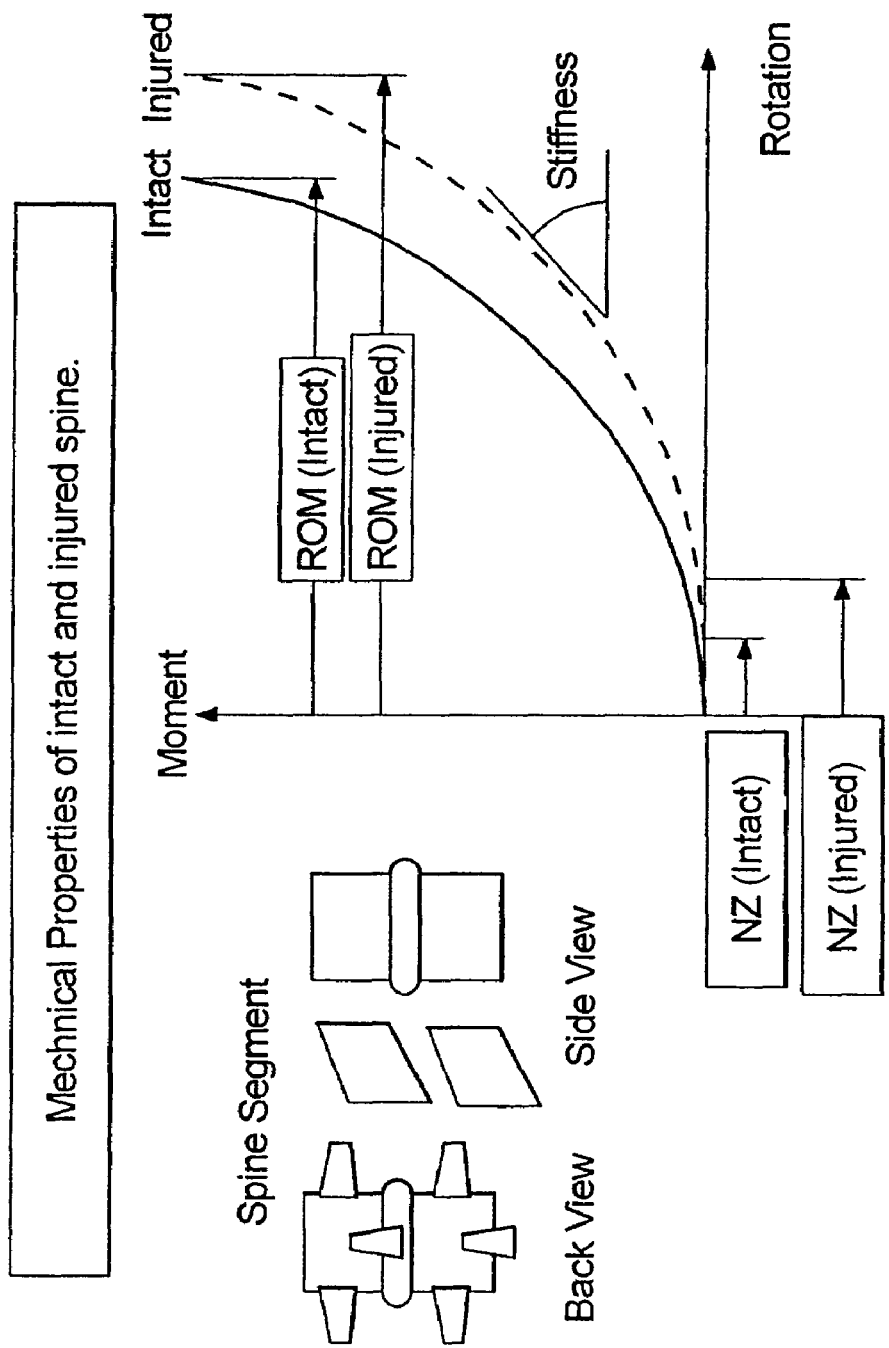
FIG. 1 is Moment-Rotation curve for a spinal segment (intact and injured), showing low spinal stiffness within a neutral zone.

In FIG. 2, the Moment-Rotation curve for a healthy spine is shown in configurations with the present stabilization device 10. This curve shows the low resistance to movement encountered in the neutral zone of a healthy spine. However, when the spine is injured, this curve changes and the spine becomes unstable, as evidenced by the expansion of the neutral zone (see FIG. 1).

In accordance with an exemplary embodiment of the present invention, people suffering from spinal injuries are best treated through the application of increased mechanical assistance in the neutral zone. As the spine moves beyond the neutral zone, the necessary mechanical assistance decreases and becomes more moderate. In particular, and with reference to FIG. 3a, the support profile contemplated in accordance with exemplary implementations of the present invention is disclosed.

Figure 3A:
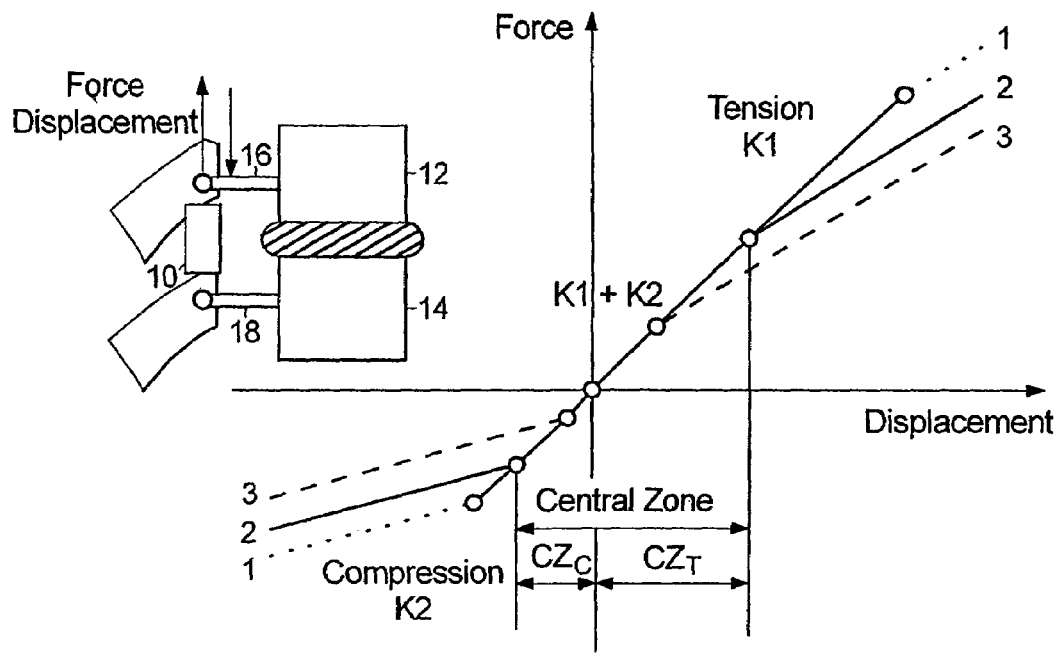
FIG. 3a is a schematic diagram of an exemplary spinal stabilization device according to the present invention in conjunction with a Force-Displacement curve, demonstrating the increased resistance provided within the central zone thereof.
Figure 3B:
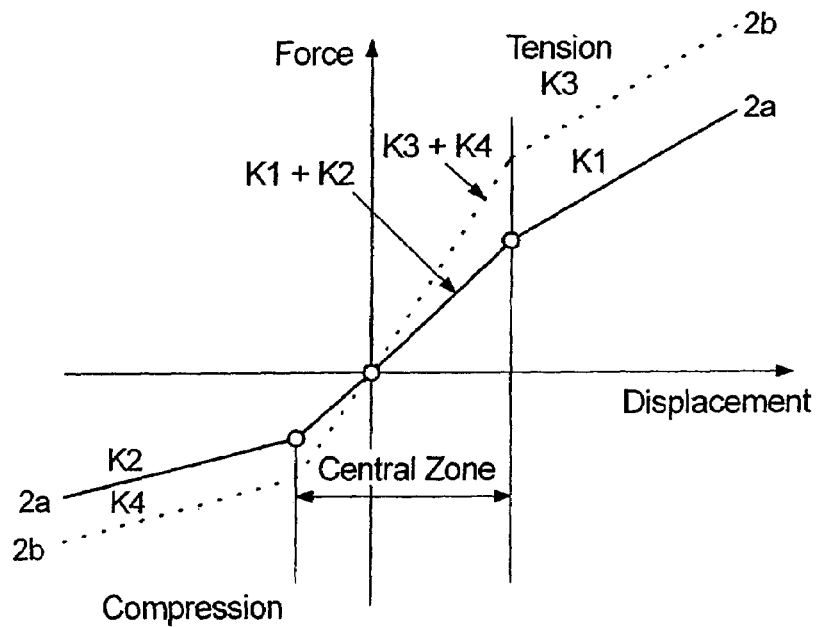
FIG. 3b is a Force-Displacement curve demonstrating the change in profile achieved through replacement of springs associated with an exemplary spinal stabilization device.
Figure 3C:
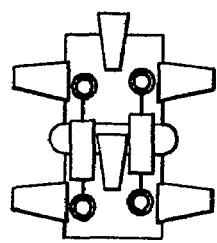
FIG. 3c is a dorsal view of the spine with a pair of spinal stabilization devices secured thereto.
Figure 3D:
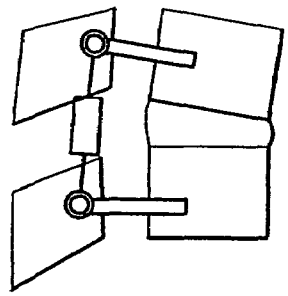
FIG. 3d is a side view showing the stabilizer in tension.
Figure 3E:
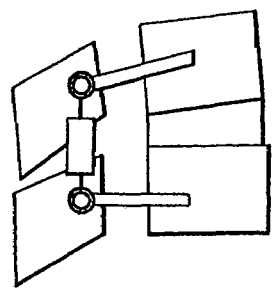
FIG. 3e is a side view showing the stabilizer in compression.

Three different profiles are shown in FIG. 3a. The disclosed profiles are merely exemplary and demonstrate the possible support requirements within the neutral zone. Profile 1 is exemplary of an individual requiring great assistance in the neutral zone, and the central zone of the stabilization device is therefore increased, providing a high level of resistance over a great displacement; Profile 2 is exemplary of an individual where less assistance is required in the neutral zone, and the central zone of the stabilization device is therefore more moderate, providing increased resistance over a more limited range of displacement; and Profile 3 is exemplary of situations where only slightly greater assistance is required in the neutral zone, and the central zone of the stabilization device may therefore be decreased to provide increased resistance over even a smaller range of displacement.

As those skilled in the art will certainly appreciate, the mechanical assistance required and the range of the neutral zone will vary from individual to individual. However, the basic tenet of the disclosed spinal stabilization systems remains; that is, greater mechanical assistance for those individuals suffering from spinal instability is required within the individual's neutral zone. This assistance is provided in the form of greater resistance to movement provided within the neutral zone of the individual and the central zone of the disclosed dynamic spine stabilization system 10.

The dynamic spine stabilization system 10 developed in accordance with the present invention generally provides mechanical assistance in accordance with the disclosed support profile. Further, in exemplary embodiments of the present disclosure, the present stabilization device 10 provides for adjustability via a concentric spring design.

More specifically, the dynamic spine stabilization system 10 provides assistance to the compromised spine in the form of increased resistance to movement (provided by springs in accordance with a preferred embodiment) as the spine moves from the neutral posture, in any physiological direction. As mentioned above, the Force-Displacement relationship provided by the dynamic spine stabilization device 10 in accordance with the present disclosure is non-linear, with greater incremental resistance around the neutral zone of the spine and central zone of the stabilization device 10, and decreasing incremental resistance beyond the central zone of the dynamic spine stabilization device 10 as the individual moves beyond the neutral zone (see FIG. 3a).

The relationship of the present stabilization device 10 to forces applied during tension and compression is further shown with reference to FIG. 3a. As discussed above, the behavior of the present stabilization device 10 is non-linear. The Load-Displacement curve has three zones: tension, central and compression. If K1 and K2 define the stiffness values in the tension and compression zones, respectively, the present stabilization device is designed such that the high stiffness in the central zone is "K1+K2". Depending upon the preload of the stabilization device 10, as will be discussed below in greater detail, the width of the central zone and, therefore, the region of high stiffness can be adjusted or refined.

Figure 4:
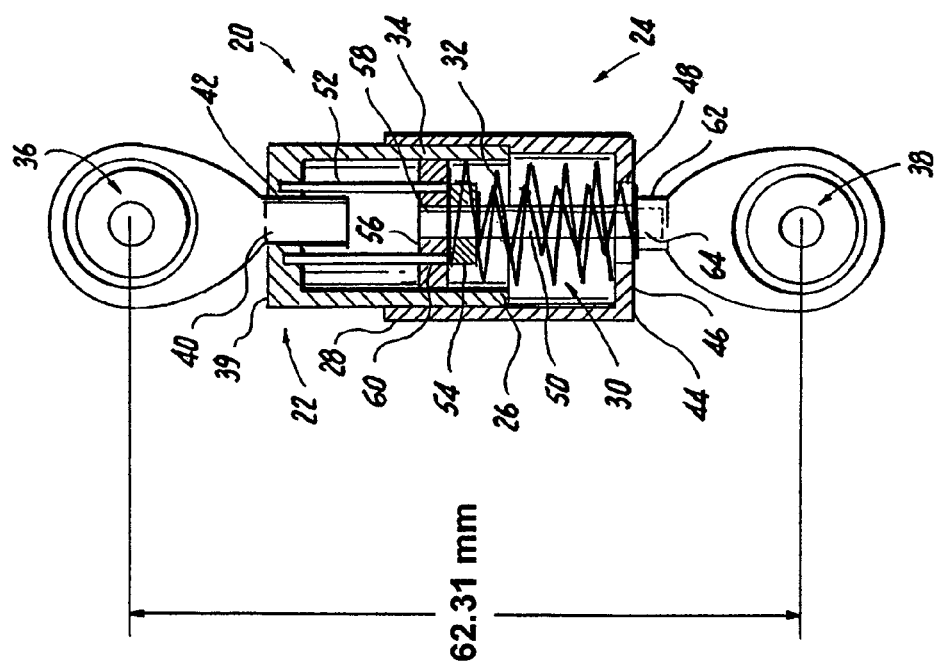
FIG. 4 is a schematic diagram of an exemplary dynamic spinal stabilization device according to the present disclosure.

With reference to FIG. 4, an exemplary dynamic spine stabilization device 10 in accordance with the present invention is disclosed. The dynamic spine stabilization device 10 includes a support assembly in the form of a housing 20 composed of a first housing member 22 and a second housing member 24. The first housing member 22 and the second housing member 24 are telescopically connected via external threads formed upon the open end 26 of the first housing member 22 and internal threads formed upon the open end 28 of the second housing member 24. In this way, the housing 20 is completed by screwing the first housing member 22 into the second housing member 24. As such, and as will be discussed below in greater detail, the relative distance between the first housing member 22 and the second housing member 24 can be readily adjusted for the purpose of adjusting the compression of the first spring 30 and second spring 32 contained within the housing 20. Although springs are employed in accordance with a preferred embodiment of the present invention, other elastic members may be employed without departing from the spirit or scope of the present invention. A piston assembly 34 links the first spring 30 and the second spring 32 to first and second ball joints 36, 38. The first and second ball joints 36, 38 are in turn shaped and designed for selective attachment to pedicle screws 16, 18 extending from the respective vertebrae 12, 14.

The first ball joint 36 is secured to the closed end 39 of the first housing member 22 via a threaded engagement member 40 shaped and dimensioned for coupling, with threads formed within an aperture 42 formed in the closed end 39 of the first housing member 22. In this way, the first ball joint 36 substantially closes off the closed end 39 of the first housing member 22. The length of the dynamic spine stabilization device 10 may be readily adjusted by rotating the first ball joint 36 to adjust the extent of overlap between the first housing member 22 and the engagement member 40 of the first ball joint 36. As those skilled in the art will certainly appreciate, a threaded engagement between the first housing member 22 and the engagement member 40 of the first ball joint 36 is disclosed in accordance with a preferred embodiment, although other coupling structures may be employed without departing from the spirit of the present invention.

The closed end 44 of the second housing member 24 is provided with a cap 46 having an aperture 48 formed therein. As will be discussed below in greater detail, the aperture 48 is shaped and dimensioned for the passage of a piston rod 50 from the piston assembly 34 therethrough.

The piston assembly 34 includes a piston rod 50 and retaining rods 52 that cooperate with first and second springs 30, 32. The piston rod 50 includes a stop nut 54 and an enlarged head 56 at its first end 58. The enlarged head 56 is rigidly connected to the piston rod 50 and includes guide holes 60 through which the retaining rods 52 extend during operation of exemplary dynamic spine stabilization device 10. As such, the enlarged head 56 is guided along the retaining rods 52 while the second ball joint 38 is moved toward and away from the first ball joint 36. As will be discussed below in greater detail, the enlarged head 56 interacts with the first spring 30 to create resistance as the dynamic spine stabilization device 10 is extended and the spine is moved in flexion.

A stop nut 54 is fit over the piston rod 50 for free movement relative thereto. However, movement of the stop nut 54 toward the first ball joint 36 is prevented by the retaining rods 52 that support the stop nut 54 and prevent the stop nut 54 from moving toward the first ball joint 36. As will be discussed below in greater detail, the stop nut 54 interacts with the second spring 32 to create resistance as the dynamic spine stabilization device 10 is compressed and the spine is moved in extension.

The second end 62 of the piston rod 50 extends from the aperture 48 at the closed end 44 of the second housing member 24, and is attached to an engagement member 64 of the second ball joint 38. The second end 62 of the piston rod 50 is coupled to the engagement member 64 of the second ball joint 38 via a threaded engagement. As those skilled in the art will certainly appreciate, a threaded engagement between the second end 62 of the piston rod 50 and the engagement member 64 of the second ball joint 38 is disclosed in accordance with a preferred embodiment, although other coupling structures may be employed without departing from the spirit or scope of the present invention.

As briefly mentioned above, the first and second springs 30, 32 are held within the housing 20. In particular, the first spring 30 extends between the enlarged head 56 of the piston rod 50 and the cap 46 of the second housing member 24. The second spring 32 extends between the distal end of the engagement member 64 of the second ball joint 38 and the stop nut 54 of the piston rod 50. The preloaded force applied by the first and second springs 30, 32 holds the piston rod in a static position within the housing, 20, such that the piston rod is able to move during either extension or flexion of the spine.

In use, when the vertebrae 12, 14 are moved in flexion and the first ball joint 36 is drawn away from the second ball joint 38, the piston rod 50 is pulled within the housing 24 against the force being applied by the first spring 30. In particular, the enlarged head 56 of the piston rod 50 is moved toward the closed end 44 of the second housing member 24. This movement causes compression of the first spring 30, creating resistance to the movement of the spine. With regard to the second spring 32, the second spring 32, which is captured between stop nut 54 and second ball joint 38, extends or lengthens as a result of movement of second ball joint 38 away from first ball joint 36. As the vertebrae move in flexion within the neutral zone, the height (or length) of the second spring 32 is increased, reducing the distractive force, and in effect increasing the resistance of the device to movement. Through this mechanism, as the spine moves in flexion from the initial position, both spring 30 and spring 32 resist the distraction of the device directly, either by increasing the load opposing the motion (i.e., first spring 30) or by decreasing the load assisting the motion (i.e., second spring 32).

However, when the spine is in extension, and the second ball joint 38 is moved toward the first ball joint 36, the engagement member 64 of the second ball joint 38 moves toward the stop nut 54, which is held in place by the retaining rods 52 as the piston rod 50 moves toward the first ball joint 36. This movement causes compression of the second spring 32 held between the engagement member 64 of the second ball joint 38 and the stop nut 54, to create resistance to the movement of the dynamic spine stabilization device 10. With regard to the first spring 30, the first spring 30 is supported between the cap 46 and the enlarged head 56 and, as the vertebrae move in extension within the neutral zone, the height of the second spring 30 is increased, reducing the compressive force and, in effect, increasing the resistance of the device to movement. Through this mechanism, as the spine moves in extension from the initial position, both spring 32 and spring 30 resist the compression of the device directly, either by increasing the load opposing the motion (i.e., second spring 32) or by decreasing the load assisting the motion (i.e., first spring 30).

Based upon the use of two concentrically positioned elastic springs 30, 32 as disclosed in accordance with exemplary embodiments of the present disclosure, an assistance (force) profile as shown in FIG. 2 is provided by the present dynamic spine stabilization device 10. That is, the first and second springs 30, 32 work in conjunction to provide a large elastic force when the dynamic spine stabilization device 10 is displaced within its central zone. However, once displacement between the first ball joint 36 and the second ball joint 38 extends beyond the central zone of the stabilization device 10 and the neutral zone of the individual's spinal movement, the incremental resistance to motion is substantially reduced as the individual no longer requires the substantial assistance needed within the neutral zone. This is accomplished by setting or defining the central zone of the stabilization device as disclosed herein. The central zone of the force displacement curve is the area of the curve which represents when both springs are acting in the device as described above. When the motion of the spine is outside the neutral zone and the corresponding device elongation or compression is outside the noted central zone, the spring which is elongating reaches its free length. Free length, as anybody skilled in the art will appreciate, is the length of a spring when no force is applied. Thus, in exemplary embodiments of the disclosed spinal stabilization device/mechanism, the central zone corresponds to a region where both springs are acting to resist motion. Outside the central zone, the resistance to movement of the device is only reliant on the resistance of one spring: either spring 30 in flexion, or spring 32 in extension.

As briefly discussed above, the dynamic spine stabilization device 10 may be adjusted by rotation of the first housing member 22 relative to the second housing member 24. This movement changes the distance between the first housing member 22 and the second housing member 24 in a manner which ultimately changes the preload placed across the first and second springs 30, 32. This change in preload alters the resistance profile of the present dynamic spine stabilization device 10; in cases where the distance is reduced, the resistance profile is changed from that shown in Profile 2 of FIG. 3a to an increase in preload (see Profile 1 of FIG. 3a) which enlarges the effective range in which the first and second springs 30, 32 act in unison. This increased width of the central zone of the stabilizer 10 correlates to higher stiffness over a larger range of motion of the spine. This effect can be reversed by increasing the distance, as is evident in Profile 3 of FIG. 3a.

Exemplary embodiments of the disclosed dynamic spine stabilization device 10 are attached to pedicle screws 16, 18 extending from the vertebral section requiring support. During surgical attachment of the dynamic spine stabilization device 10, the magnitude of the stabilization device's central zone can be adjusted for each individual patient, as judged by the surgeon and/or quantified by an instability measurement device. This adjustable feature of the disclosed dynamic spine stabilization device 10 is exemplified in the three explanatory profiles that have been generated in accordance with an exemplary embodiment of the present invention (see FIG. 2; note the width of the central zones of the respective devices).

Pre-operatively, the first and second elastic springs 30, 32 of the dynamic spine stabilization device 10 can be replaced by a different set to accommodate a wider range of spinal instabilities. As expressed in FIG. 3b, Profile 2b demonstrates the force displacement curve generated with a stiffer set of springs when compared with the curve shown in Profile 2a of FIG. 3b.

Intra-operatively, the length of the dynamic spine stabilization device 10 may be adjustable by turning the engagement member 40 of the first ball joint 36 to lengthen the stabilization device 10 in order to accommodate different patient anatomies and desired spinal posture. Pre-operatively, the piston rod 50 may be replaced with a piston rod of differing geometry to accommodate an even wider range of anatomic variation.

Exemplary embodiments of the disclosed dynamic spine stabilization device 10 have been tested alone to determine load-displacement relationships. When applying tension, the dynamic spine stabilization device 10 demonstrated increasing resistance up to a pre-defined displacement, followed by a reduced rate of increasing resistance until the device reached its fully elongated position. When subjected to compression, the dynamic spine stabilization device 10 demonstrated increasing resistance up to a pre-defined displacement, followed by a reduced rate of increasing resistance until the device reached its fully compressed position. Therefore, the dynamic spine stabilization device 10 exhibits a load-displacement curve that is non-linear, with the greatest resistance to displacement offered around the neutral posture. This behavior helps to normalize the load-displacement curve of a compromised spine.

Figure 5:
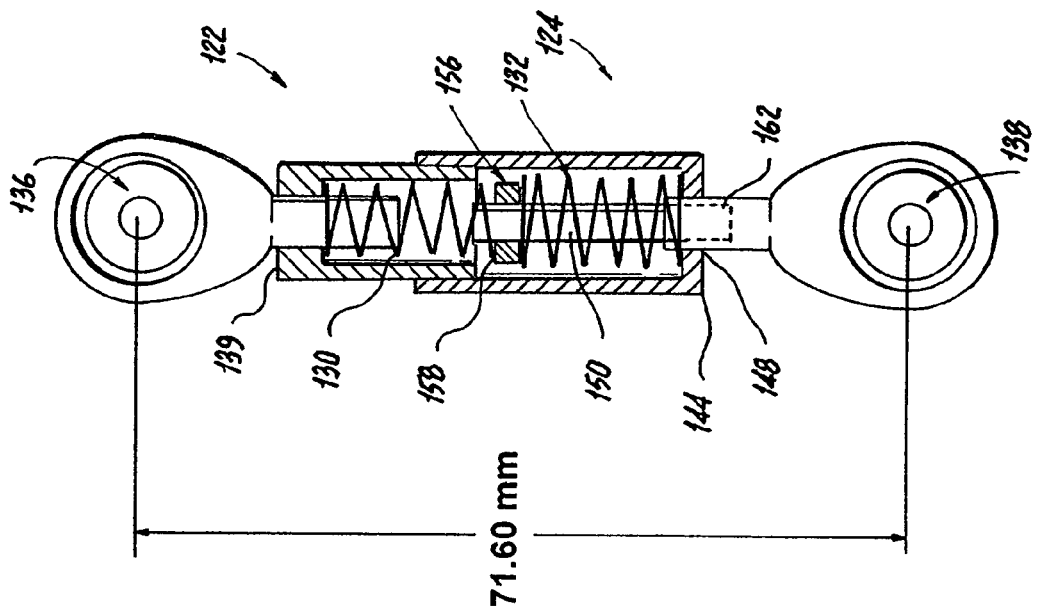
FIG. 5 is a schematic diagram of an alternate dynamic spinal stabilization device in accordance with the present disclosure.

In another exemplary embodiment of the advantageous spinal stabilization designs of the present disclosure and with reference to FIG. 5, the stabilization device 110 may be constructed with an in-line spring arrangement. In accordance with this embodiment, the housing 120 is composed of first and second housing members 122, 124 which are coupled with threads allowing for adjustability. A first ball joint 136 extends from the first housing member 122. The second housing member 124 is provided with an aperture 148 through which the second end 162 of piston rod 150 extends. The second end 162 of the piston rod 150 is attached to the second ball joint 138. The second ball joint 138 is screwed onto the piston rod 150.

The piston rod 150 includes an enlarged head 156 at its first end 158. The first and second springs 130, 132 are respectively secured between the enlarged head 156 and the closed ends 139, 144 of the first and second housing members 122, 124. In this way, the stabilization device 110 provides resistance to both expansion and compression using the same mechanical principles described for the previous exemplary embodiment.

Adjustment of the resistance profile in accordance with this alternate embodiment may be achieved by rotating the first housing member 122 relative to the second housing member 124. Rotation in this way alters the central zone of high resistance provided by the stabilization device 110. As previously described, one or both springs may also be exchanged to change the slope of the force-displacement curve in two or three zones respectively.

Figure 6:
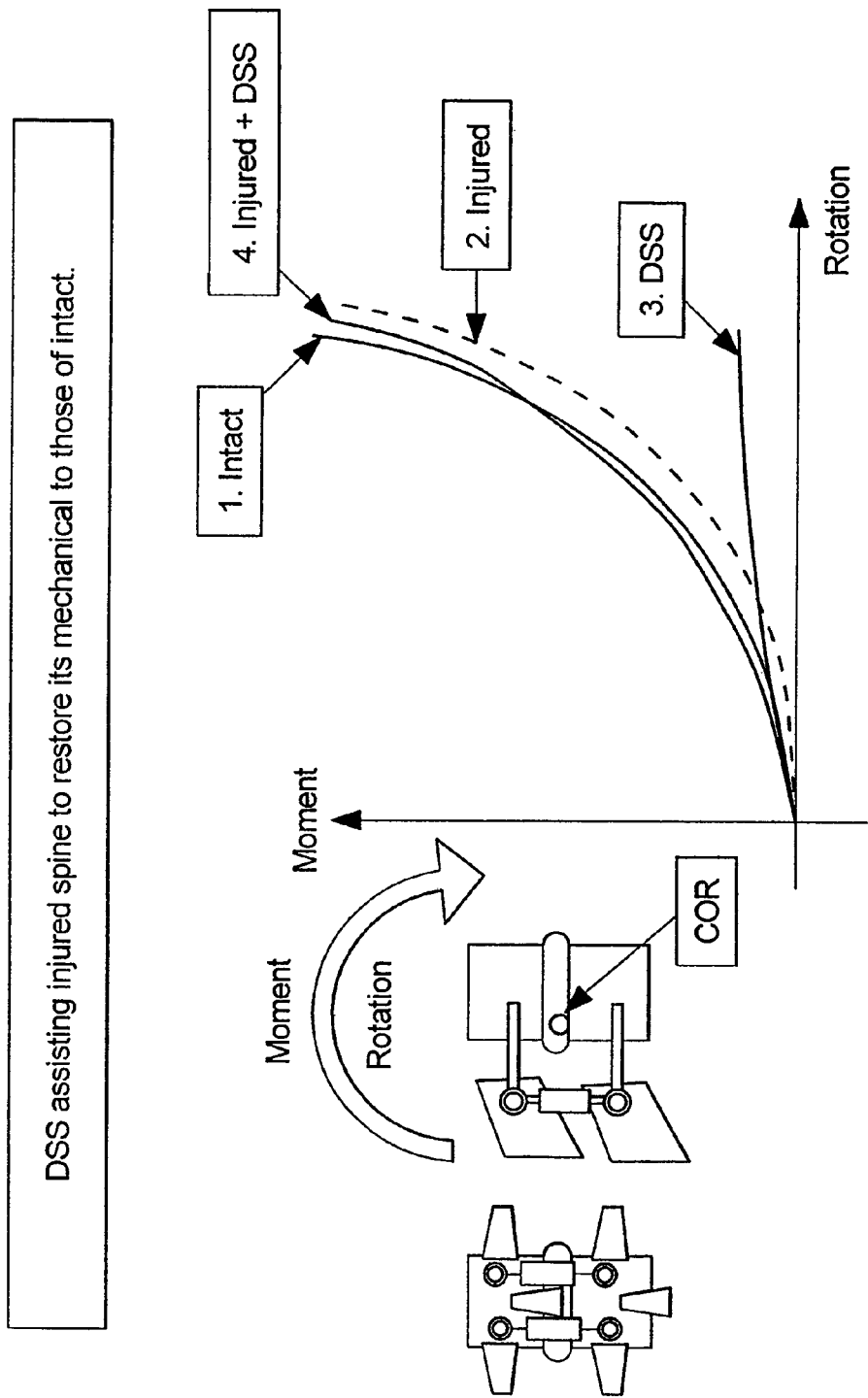
FIG. 6 is a Moment-Rotation curve demonstrating one aspect of the manner in which the disclosed spinal stabilization device assists spinal stabilization.

To explain how the stabilization devices 10, 110 assist a compromised spine (increased neutral zone), reference is made to the moment-rotation curves of FIG. 6. Four curves are shown: 1. Intact, 2. Injured, 3. Stabilizer and, 4. Injured+ Stabilizer. These are, respectively, the Moment-Rotation curves of the intact spine, injured spine, stabilization device alone, and stabilization device plus injured spine. It is noted that the fourth curve is close to the intact curve. Thus, the stabilization device, which provides greater resistance to movement around the neutral posture, is ideally suited to compensate for the instability of the spine.

In addition to the dynamic spine stabilizer described above, other complementary devices are contemplated. For example, a link-device may be provided for joining the left- and right-stabilization units to help provide additional stability in axial rotation and lateral bending. This link-device will be a supplement to the disclosed dynamic spine stabilization devices. The link-device may be applied as needed on an individual patient basis. In addition, a spinal stability measurement device may be utilized. The measurement device may be used to quantify the stability of each spinal level at the time of surgery. The disclosed measurement device may be attached intra-operatively to a pair of adjacent spinal components at compromised and uncompromised spinal levels to measure the stability of each level. The stability measurements of the adjacent uninjured levels relative to the injured level(s) can be used to determine the appropriate adjustment of the disclosed spinal stabilization device. Additionally, the stability measurements of the injured spinal level(s) can be used to adjust the device by referring to a tabulated database of normal, uninjured spinal stabilities. The disclosed measurement device will be simple and robust, so that the surgeon is provided with the information in the simplest possible manner under operative conditions.

The choice of springs used in accordance with the spinal stabilization devices of the present invention to achieve the desired force profile curve is generally governed, at least in part, by the basic physical laws governing the force produced by springs. In particular, the force profile described above and shown in FIG. 3a is achieved through the unique design of the present stabilization device rather than unique properties of individual spring components or other elastic members.

The stabilization device of the present disclosure advantageously functions both in compression and tension, even though the two springs within the stabilization device are both of compression type. Second, the higher stiffness ($K_1+K_2$) provided by the disclosed stabilization device in the central zone is due to the presence of a preload. Both springs are made to work together when the preload is present. As the stabilization device is either tensioned or compressed within the central zone, the force increases in one spring and decreases in the other. When the decreasing force reaches the zero value, the spring corresponding to this force no longer functions, thus decreasing the stabilization function.

Figure 7A:
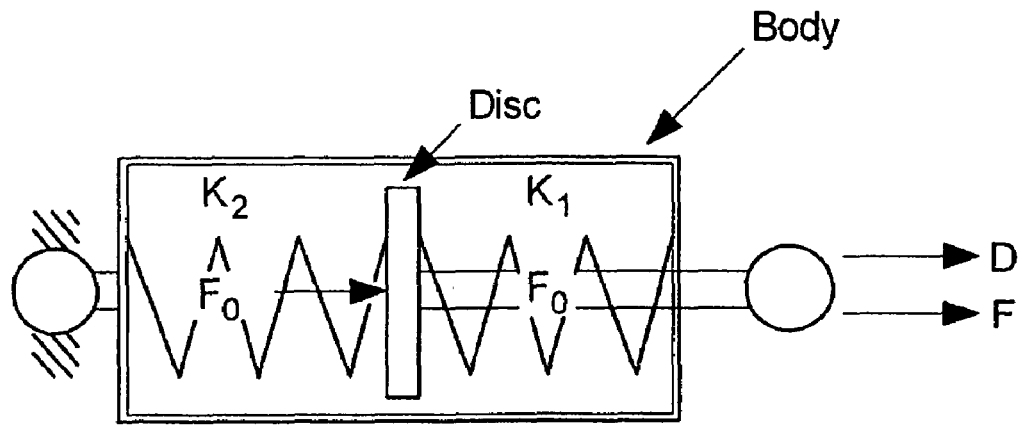
FIGS. 7a and 7b are respectively a free body diagram of an exemplary spinal stabilization device according to the present disclosure, and a diagram representing a central zone of the spinal stabilization device.
Figure 7B:
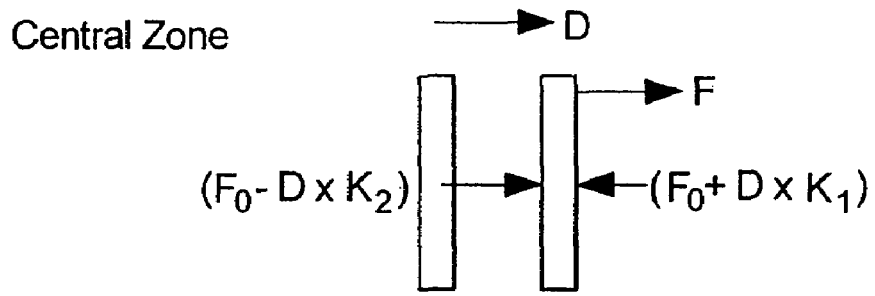

An engineering analysis, including the diagrams shown in FIGS. 7a and 7b, is presented below. The analysis specifically relates to the exemplary embodiment disclosed in FIG. 5, although those skilled in the art will appreciate the way in which the present engineering analysis applies to all embodiments disclosed in accordance with the present invention.

$F_0$ is the preload within the stabilization device, introduced by shortening the body length of the housing as discussed above.

$K_1$ and $K_2$ are stiffness coefficients of the compression springs, active during stabilization device tensioning and compression, respectively.

F and D are, respectively, the force and displacement of the disc of the stabilization device with respect to the body of the stabilization device.

The sum of forces on the disc must equal zero. Therefore, $$F+(F_0-D\times K_2)-(F_0+D\times K_1)=0, \text{ and}$$

$$F=D\times(K_1+K_2).$$

With regard to the central zone (CZ) width (see FIG. 3a):
On Tension side $CZ_T$ is:

$CZ_T = F_0/K_2$.

On Compression side $CZ_T$ is:

$CZ_C = F_0/K_1$.

In a broader sense, the present disclosure provides a spinal stabilization device, system and/or apparatus (and associated method(s)) that deliver desirable levels of stabilization to a spine while maintaining or preserving physiologically desirable levels and/or degrees of spinal motion. Thus, while providing spinal stabilization, it is also highly desirable to permit substantially unrestricted angular motion for the spine. Indeed, a patient's unhindered ability to "bend over" with minimal effect on spinal loading despite the introduction of a spinal stabilization device, system and/or apparatus is of primary clinical significance.

The positioning of a spinal stabilization device posterior to the spine has the effect of repositioning the "center of rotation" for that segment of the spine in a posterior direction from its normal anatomical location, i.e., toward the stabilization device. As used herein, the term "center of rotation" refers to a moving point or axis around which the spine rotates as the spine moves in flexion and/or tension. Indeed, a non-dynamic spinal stabilization device that is positioned in a posterior direction relative to the spine, e.g., a rigid rod extending between adjacent pedicle screws, will necessarily move the center of rotation for that spinal segment in a posterior location to be substantially coincident with the stabilization device.

Like a teeter-totter, the axis of rotation is dictated by the center of resistive balance between the anterior and posterior anatomy of the spine. Stabilization of the spine requires imparting increased resistance similarly to placing a large person behind a small child on a teeter-totter. Therefore, much like moving the pivot point of a teeter-totter, a spinal stabilization device is ideally designed so as to rebalance the spine. In this example, the axis of rotation of the teeter-totter would need to be moved closer to the child and large person to resume normal function. As the teeter-totter example clearly demonstrates, the travel and mechanics of a dynamic system, like the spine, are significantly altered with the addition of the increased resistance.

Posterior translation of the center of rotation is generally disadvantageous because, as the center of rotation is moved from its normal anatomical location to a posterior location, the patient's ability to achieve a given level of angular motion requires a greater degree of travel in the region of the spine anterior to the new axis of rotation. Stated differently, for a given amount of spinal extension/travel, a greater force will be exerted on the anterior aspect of the spine if the center of rotation has been moved to a posterior location relative to its normal anatomical location. This fundamental biomechanical relationship is explained by the greater moment arm that is available for angular motion when the center of rotation is at (or substantially near) its normal anatomical location. By moving the center of rotation to a posterior location, e.g., by introducing a rigid spinal stabilization device to such posterior location, the moment arm is substantially reduced, thereby restricting the availability of "normal" angular motion for the patient.

Of course, in the absence of a spinal stabilization device, the center of rotation for a given spinal segment will remain in its normal anatomical location. However, this approach to maintaining a desired level of angular motion is generally not available to a patient requiring spinal stabilization due to injury, disease or the like. Thus, in an ideal situation, the spinal stabilization device would provide the necessary force(s) to stabilize the spine, while simultaneously minimizing the degree to which the center of rotation for the treated spinal segment is relocated from its normal anatomical location. Indeed, it is highly desirable to achieve a requisite amount or level of spinal stabilization, while having a limited or negligible impact on the center of rotation for such spinal segment.

According to exemplary embodiments of the present disclosure, these clinically desirable results have been found to be achieved by providing a spinal stabilization device, system or apparatus that provides a predetermined level of resistance while simultaneously accommodating a predetermined travel distance (i.e., linear travel ($\Delta x$) between adjacent pedicles), such spinal stabilization device, system or apparatus also having a minimal impact on the location of the center of rotation for the spinal segment being treated. In exemplary embodiments of the present disclosure, the foregoing advantageous clinical results have been achieved by providing a dynamic stabilization device, system or apparatus that is adapted for posterior placement, the stabilization device being adapted to provide a predetermined level of resistance in the range of about 150 to about 450 lbs/inch, and preferably between about 200 and about 400 lbs/inch, and permitting a predetermined travel distance of about 1.5 mm and about 5 mm, and preferably between about 2 mm and about 4 mm.

By providing resistance in the noted range and restricting the travel distance to the noted range, it has been found that the disclosed stabilization device provides a desired level of stabilization, as reflected by range of motion values that closely approximate pre-injury range of motion levels. In addition, the foregoing resistance levels are not so high as to alter the location of the center of rotation of the treated spinal segment from its normal anatomical location to levels previously obtained, thereby permitting substantially unimpeded angular motion despite the posterior presence of a stabilization device. Thus, the disclosed dynamic spinal stabilization devices, systems and apparatus successfully address all conflicting aspects of spinal stabilization treatments, and provide advantageous clinical results that are reflected in desired range of motion and angular motion attributes.

According to exemplary embodiments of the present disclosure, the advantageous resistance/travel parameters set forth herein may be achieved in a variety of ways. Thus, for example, one or more springs may be positioned with respect to a pair of pedicle screws so as to impart the desired level of resistance, i.e., between about 150 lbs/inch and about 450 lbs/inch. The one or more springs may also be mounted, staked and/or otherwise captured with respect to the pedicle screws in a manner that limits the available travel to the desired range, i.e., about 1.5 to about 5 mm. In an alternative implementation of the present disclosure, one or more non-spring elastic members may be positioned with respect to a pair of pedicle screws so as to impart the desired level of resistance, and appropriate mechanical means (e.g., one or more stops) may be associated with the spinal stabilization device, system or apparatus to limit the travel distance to the desired range. In still further exemplary embodiments of the present disclosure, a plurality of spinal stabilization systems, devices and/or apparatus are combined (e.g., in series or in parallel) to deliver the desired resistance/travel performance parameters. Thus, for example, a first stabilization component may be provided that includes one or more springs, and a second stabilization component that includes one or more non-spring elastic members may be positioned in parallel (or in series) with respect to a pair of pedicle screws so as to deliver total resistance of about 150 lbs/inch to about 450 lbs/inch and so as to accommodate travel of about 1.5 mm to about 5 mm.

It has been found according to the present disclosure that operating outside the resistance and travel ranges set forth herein is disadvantageous for purposes of spinal stabilization. More particularly, stabilization devices that impart resistance of less than about 150 lbs/inch have been found to provide inadequate spinal stabilization. Conversely, stabilization devices that impart resistance of greater than about 450 lbs/inch have been found to provide limited incremental stabilization effect, while undesirably increasing the rigidity of the stabilization device and moving the center of rotation in a posterior direction from its normal anatomical location, thereby increasing the amount of anterior motion necessary to obtain said motion and unnecessarily compromising normal spinal biomechanics. In like manner, stabilization devices that limit the relative travel between adjacent pedicles, i.e., $\Delta x$, to less than about 1.5 mm to preclude desirable levels of physiologic spinal motion, while spinal stabilization devices that permit relative travel between adjacent pedicles of greater than about 5 mm permit spinal motion that exceeds that which is necessary to provide sufficient stabilization.

In short, spinal stabilization systems, devices and apparatus (and associated methods) that that deliver desirable levels of stabilization to a spine (resistance of between about 150 lbs/inch and 450 lbs/inch) while maintaining or preserving physiologically desirable levels of spinal motion (travel of about 1.5 mm to about 5 mm) offer highly advantageous spinal stabilization. In addition, by providing advantageous levels of spinal stabilization as described herein, it is further believed that the load experienced by pedicle screws associated with the disclosed spinal stabilization system, device or apparatus is reduced, thereby reducing the potential for pedicle screw failure.

Additional Experimental Results

To evaluate a stabilization device according to the present disclosure, cadaver response to applied moments in predetermined modalities was tested. In particular, measurements were made with respect to range of motion (ROM), neutral zone (NZ) and a high flexibility zone (HFZ). The experimental study was undertaken to determine whether a stabilization device according to the present disclosure is effective in reducing spinal instability (measured as a reduction in NZ and HFZ), while allowing normal ROM.

Study Design and Setting: The characteristics of five (5) cadaveric motion segments were evaluated in five (5) states: (i) intact; (ii) nucleotomy (N); (iii) nucleotomy plus stabilization device; (iv) laminectomy with partial facetectomy (LPF); and (v) LPF plus stabilization device. Each injury was chosen based on its history of use and clinical significance. Five human lumbar cadaver specimens were used, namely four L3-4 segments and one L1-2 segment.

Methods: Specimens were obtained within 24 hours of death and stored in saline soaked gauze at −20° C. until the time of testing. The specimens were thawed and extraneous tissue removed. Plain radiographs were taken of the spines to determine anatomy, degree of disc degeneration and pre-existing bony pathology (if any). Specimens with pathology (e.g., bridging osteophytes, Schmol's nodes or obvious facet degeneration) were excluded from the study. Specimens with significant pre-existing disc pathology (such as herniation) were also excluded from the study.

Pedicle screws were placed bilaterally in the inferior and superior vertebral bodies. Additional augmentation of pedicle screw fixation was achieved by removing the pedicle screw, adding a small amount of epoxy ($\approx$1 cc), and reinserting the screw. Pedicle screws were wrapped in saline soaked paper and each motion segment was potted in low melting temperature alloy. The construct was placed in test equipment adapted to provide multiple degrees of freedom. The potting fixture was bolted to the testing machine such that the specimen was rigidly attached relative to the machine. The inferior fixture rested on an x-y table which allowed the specimen unconstrained free motion during testing.

A six-axis load cell (AMTI, Inc., Watertown, Mass.) was used to measure the forces and torques applied to the specimen during testing. An axial compressive load was applied continuously to the specimen (preload of 200N), while pure bending moments in flexion/extension, left/right lateral bending, and left/right torsion were applied to the superior vertebral body of the specimen. Relative changes in position and angulation were measured with high-resolution optical encoders (Gurley Precision Instruments, Troy, N.Y.). Displacement of the stabilization device between the pedicle screws was measured using two position transducers (SpaceAge Control, Palmdale, Calif.). Data were collected at a minimum sampling rate of 10 Hz.

Intact specimens (no injury and no stabilization) were loaded through three cycles each to 10 Nm in flexion/extension, left/right lateral bending, and left/right torsion at 1 mm/minute with a continuous 200 N axial compressive preload. Following completion of intact testing, specimens were removed from the test machine. Following placement of the stabilization device/system of the present disclosure, specimens were placed back into the test machine and the test protocol was repeated. In the tests described herein, a stabilization device of the type depicted in FIG. 5. Each motion segment was again loaded through 3 cycles of forward flexion/extension, left/right lateral bending, and left/right torsion under a continuous compressive 200 N axial compressive pre-load. Testing was repeated under the following conditions: (i) nucleotomy with no stabilization, nucleotomy with stabilization, laminectomy with partial facetectomy (LPF) with no stabilization, and LPF with stabilization.

Outcome Measures: Following the completion of the testing, raw data text files were exported to a Microsoft Excel program. Data included cycle number, motion, current angle, current moment, axial load, displacement transducer on right side, and displacement transducer on left side. Range of motion at 10 Nm, neutral zone at 2.5 Nm (high flexibility zone), neutral zone at 0.2 Nm (passive curve), and displacement of the pedicle screws of the uninstrumented constructs (i.e., in the absence of a dynamic stabilization device according to the present disclosure) were compared to the instrumented constructs (i.e., with a dynamic stabilization device according to the present disclosure). ROM, NZ and HFZ were reported for Flexion/Extension, Lateral Bending and Axial Rotation. ROM=rotation±10N-m; NZ=rotation±0.2 Nm of the passive response prior to crossing the zero moment axis; HFZ=rotation±2.5 Nm on the active curve.

Figure 8:
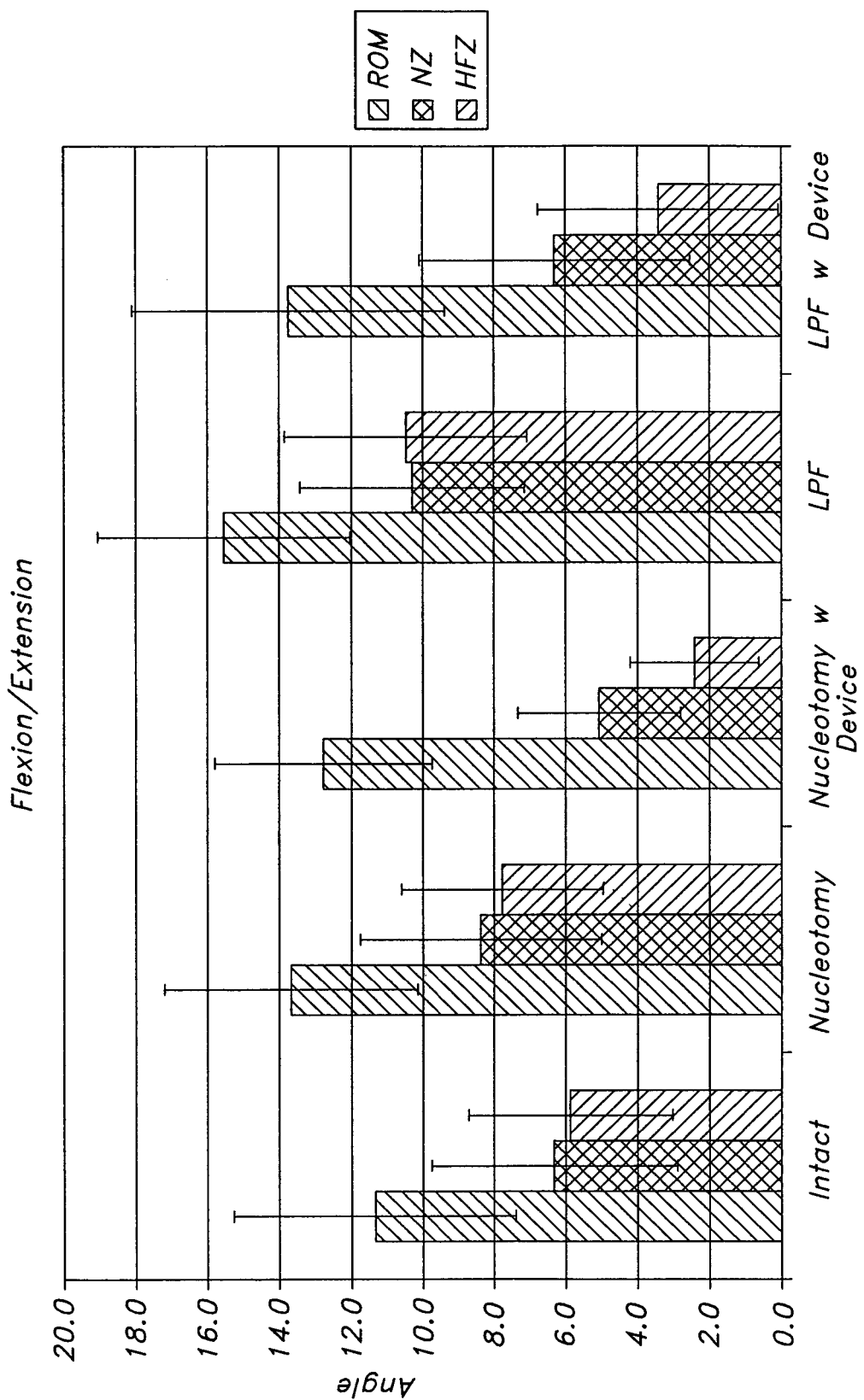
FIG. 8 is a bar graph reflecting flexion/extension data based on cadaver studies that included an exemplary dynamic spinal stabilization device according to the present disclosure.
Figure 9:
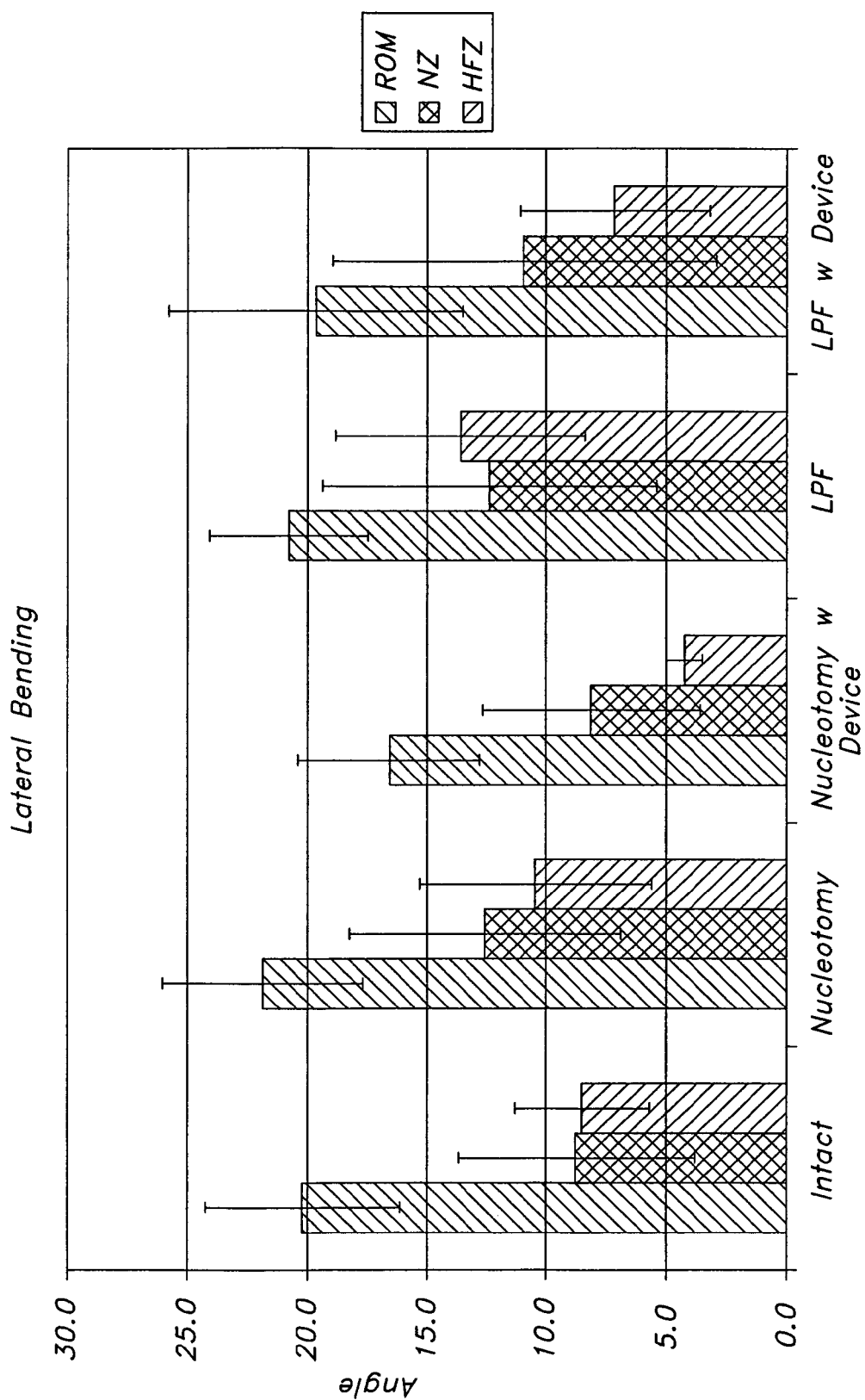
FIG. 9 is a bar graph reflecting lateral bending data based on cadaver studies that included an exemplary dynamic spinal stabilization device according to the present disclosure.
Figure 10:
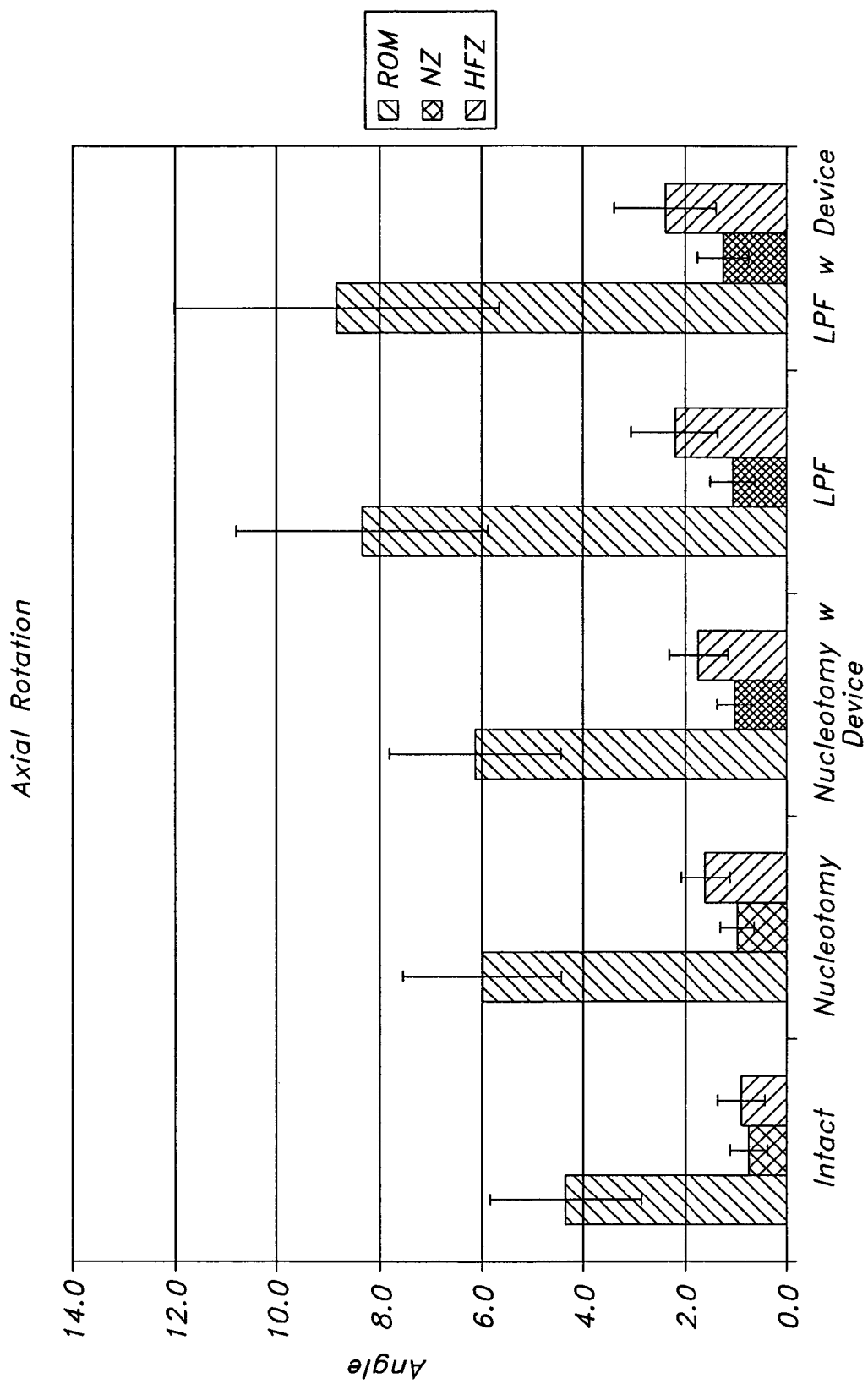
FIG. 10 is a bar graph reflecting axial rotation data based on cadaver studies that included an exemplary dynamic spinal stabilization device according to the present disclosure.

Results: Due to specimen degradation, two (2) specimens were not evaluated in LPF and LPF plus stabilization device. Mean range of motion, neutral zone and displacement data for each construct in flexion/extension, lateral bending, and axial rotation are set forth in the bar graphs of FIGS. 8-10. As the bar graphs show, spinal instability increases with surgical injury. This may be measured as an increase in ROM and a significantly higher relative increase in NZ and HFZ. Through use of the disclosed stabilization device as described herein, it was possible to advantageously reduce NZ and HFZ to levels that are comparable to intact levels, while simultaneously leaving ROM uncompromised.

Figure 11:
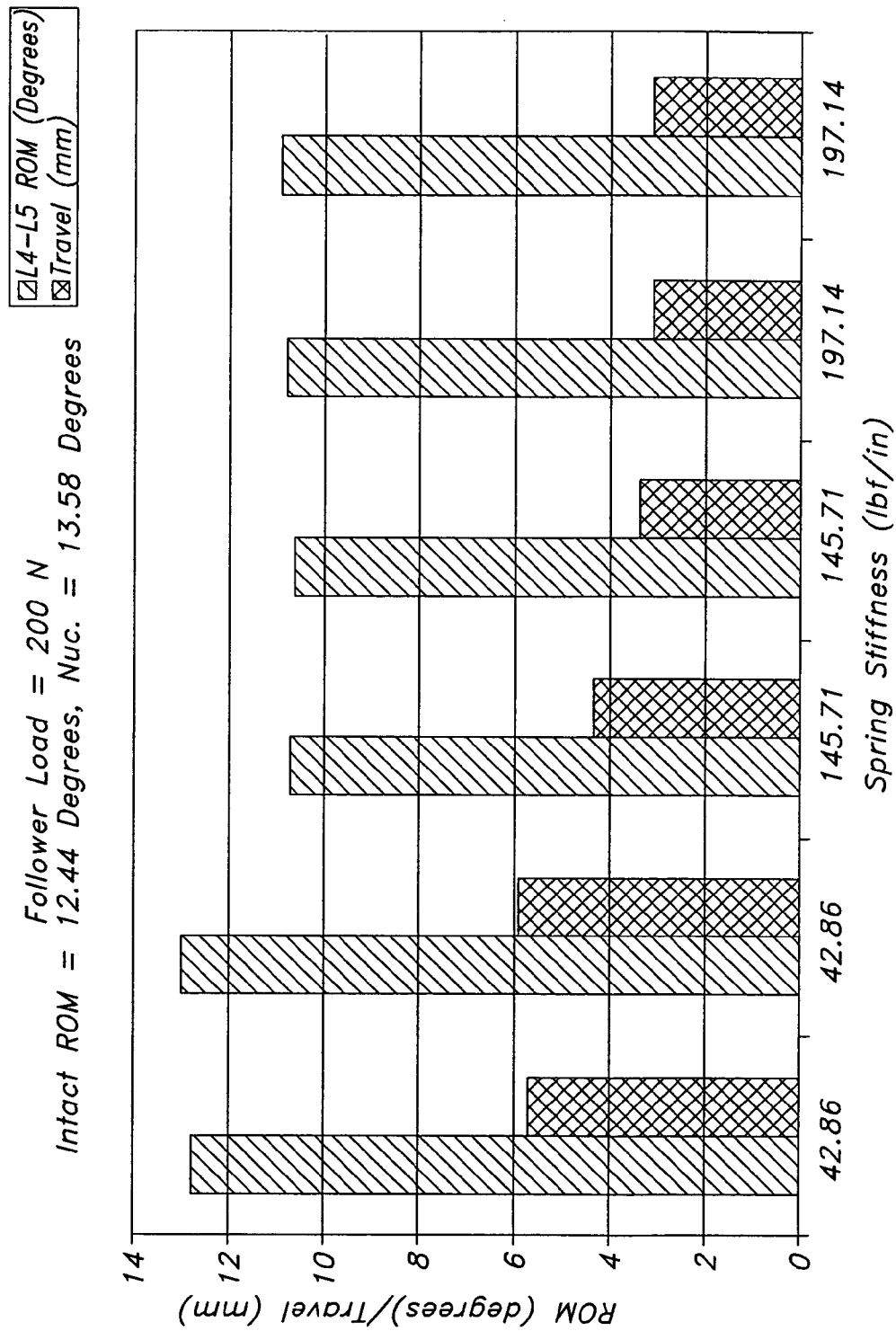
FIG. 11 is a bar graph reflecting range of motion (ROM) and travel for a plurality of dynamic stabilization systems.
Figure 12:
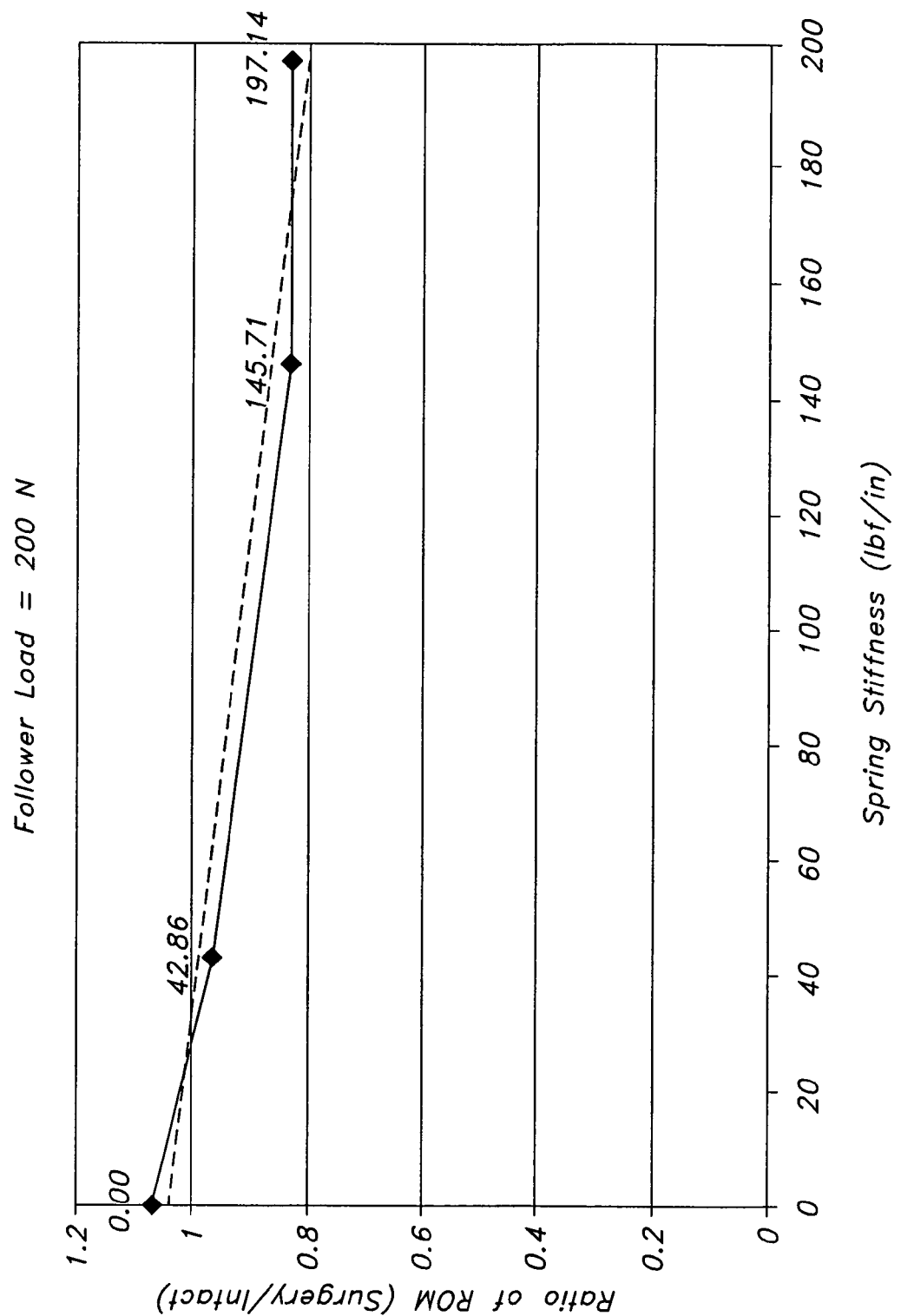
FIG. 12 is a plot of a range of motion (ROM) ratio versus spring stiffness for dynamic stabilization systems.

Further Test Results:

With reference to FIGS. 11 and 12, data supporting the criticality described herein with respect to resistance/travel parameters was generated in separate testing from that described above, and such data is provided in bar chart and graphical form for two distinct specimens. With initial reference to FIG. 11, a series of spring stiffnesses were tested in the L4-L5 spinal region using a spinal stabilization device according to the present disclosure. In particular, a spinal stabilization device of the type described with reference to FIGS. 4 and 5 was employed in cadaver studies to generate the data reflected in FIGS. 11 and 12. Accordingly, the spinal stabilization device included first and second nested springs that were subjected to a preload of 200 N. Of note, additional studies were performed with a preload of 400 N with consistent results. The tested spinal segment showed an intact range of motion (ROM) of 12.44 degrees and an injured ROM (i.e., ROM post-nucleotomy) of 13.58 degrees.

The spring stiffnesses set forth along the X-axis of the bar graphs of FIG. 11 reflect the spring forces tested in the outer spring position. The outer spring corresponds to the "flexion" spring in the disclosed spinal stabilization device of FIGS. 4 and 5, and represents the dominant spring for purposes of characterizing the performance of the disclosed spinal stabilization device. Experimental data has been generated with a relative spring stiffness of 20:10 and 10:20 between the inner and outer springs, with comparable results. The data reported herein corresponds to tests wherein the relationship between the outer spring stiffness (flexion spring) and the inner spring stiffness (tension spring) was 20:10. Thus, in the data reported on FIG. 11, three distinct spring stiffnesses were tested for the flexion spring in an exemplary spinal stabilization device of the present disclosure, with each spring stiffness tested in duplicate test runs. Data was collected for ROM (in degrees; left-most bar in each pair), and travel distance (in mm; right-most bar in each pair). Travel distance refers to the distance that the first and second pedicle screws travel with respect to each other and is an indicia of the degree to which the axis of rotation of the spine is effected by a spinal intervention. As the travel distance is reduced, greater compromise of the normal motion of the spine arises.

With initial reference to the bar graphs associated with a spring stiffness of 42.86 lbf/in, it is noted that the ROM exceeds the ROM associated with an intact spine. Thus, with a spine stiffness of 42.86 lbf/in for the outer spring, the disclosed spinal stabilization device provides insufficient stabilization forces to reduce the ROM from the injured level (13.58 degrees) to the intact level (12.44). Instead, the ROM remains above 12.8 degrees (12.81 and 13.04 degrees), which corresponds to an undesirable level of spinal instability. The travel distances associated with tests wherein the outer spring had a stiffness of 42.86 lbf/in were 5.69 and 5.92 mm.

Turning to the middle two bar graphs, data is presented for test runs employing an outer spring having a stiffness of 145.71 lbf/in. For these test runs, the ROM was advantageously reduced to a level that was below the intact ROM, i.e., 10.73/10.67 degrees vs. 12.44 degrees. This reduction in ROM reflects a desirable level of stabilization. A concomitant reduction in travel distance was noted relative to the weaker spring (42.86 lbf/in). More particularly, the travel distance was reduced to 4.34/3.39 mm, reflecting an increase in the degree to which a patient's angular motion would be restricted relative to the weaker spring.

Turning to third outer spring reflected in the test data of FIG. 11, an outer spring having a stiffness of 197.14 lbf/in was tested in a spinal stabilization device of the present disclosure. Significantly, the ROM was substantially unchanged relative to the weaker spring (145.71 lbf/in), while the travel distance demonstrated further reductions (3.08/3.13 mm vs. 4.34/3.39 mm). The test data of the right-most bar graphs reflects a surprising result in spinal stabilization applications, namely that a threshold is reached wherein further increases in spring stiffness (i.e., stabilizing force) does not effect a material reduction in ROM, while continued reductions in travel distance are observed.

In view of the surprising results reported herein, clinically advantageous spinal stabilization devices/systems according to the present disclosure are characterized in that they supply a stabilizing force that substantially corresponds to the threshold level noted herein, thereby limiting the degree to which travel distance between adjacent pedicles is restricted/reduced. By minimizing the impact on travel distance, spinal stabilization devices/systems of the present disclosure advantageously permit substantially unrestricted angular motion of the spine, while delivering desired/necessary levels of spinal stabilization.

With reference to the graph of FIG. 12, further data supporting the surprisingly advantageous results achieved through the disclosed spinal stabilization devices/systems is provided. The Y-axis of FIG. 12 corresponds to a ratio of the ROM for an injured spine relative to an intact spine. Thus, if the injured spine was stabilized to its initial intact ROM performance, a ratio of 1.0 would be achieved. For clinically desirable spinal stabilization, the target ROM ratio in the test protocols described herein is 0.8. Stated differently, a desirable spinal stabilization device/system will reduce the ROM of an injured spine to a level that is approximately 80% of the initial intact ROM level.

With particular reference to FIG. 12, the initial data point (spring stiffness of 0) corresponds to test data wherein the injured ROM is approximately 10% greater than the intact ROM. Additional ROM ratio data points are provided for spring stiffnesses of 42.86 lbf/in, 145.71 lbf/in and 197.14 lbf/in. Of note, a plateau is established at an ROM ratio of about 0.82, which closely approximates the target ROM ratio of 0.8. Thus, the plot of FIG. 12 further demonstrates that additional increases in spring stiffness beyond that necessary to achieve a ROM ratio of about 0.82 is ineffective to further reduce the ROM ratio to any appreciable degree. The test results reflected in FIG. 12, and particularly the plateau, are not predicted by a least squares fit of the initial data points, as reflected by the white line charted on FIG. 12.

Based on the foregoing test results, it is apparent that advantageous spinal stabilization results may be achieved according to the present disclosure by providing spinal stabilization devices/systems that operate at the ROM ratio plateau described herein. It has been found according to the present disclosure is achieved by impart a resistance of about 150 lbs/inch to about 450 lbs/inch, and permitting a travel of about 1.5 mm to about 4.5 mm. The foregoing spinal stabilization devices/systems are generally effective to achieve an ROM ratio that closely approximates 0.8, thereby achieving advantageous levels of stabilization while simultaneously providing substantially unrestricted angular motion of the spine.

As those skilled in the art will certainly appreciate, the concepts underlying the present invention may be applied to other medical procedures. As such, these concepts may be utilized beyond spinal treatments without departing from the spirit of the present invention. While preferred and exemplary embodiments have been shown and described herein, it will be understood that there is no intent to limit the invention by such disclosure, but rather, the present disclosure is intended to encompass all modifications and alternate constructions falling within the spirit and scope of the invention as defined in the appended claims. Indeed, alternative dynamic spinal stabilization devices for use according to the present disclosure are described in a commonly assigned U.S. patent application entitled "Systems and Methods for Spine Stabilization Including a Dynamic Junction," filed on Dec. 31, 2004 and assigned Ser. No. 11/027,269, the entire contents of which are incorporated herein by reference.

The invention claimed is:

1. A dynamic stabilization system, comprising:
a stabilizing member that includes a first spring and a second spring, the stabilizing member being mounted with respect to first and second pedicle screws, wherein said first and second springs together deliver a force of between about 150 lbs/inch and 450 lbs/inch with respect to the first and second pedicle screws, and restrict the relative travel distance between the first and second pedicle screws to a distance of between about 1.5 mm and 5 mm.

2. The dynamic stabilization system according to claim 1, wherein said first and second springs are in a nested orientation.

3. The dynamic stabilization system according to claim 1, wherein said first and second springs are in an axially aligned orientation.

4. The dynamic stabilization system according to claim 1, wherein said stabilizing member includes a housing within which are positioned said first and second springs.

5. The dynamic stabilization system according to claim 4, wherein said housing includes first and second housing members, and wherein said first and second housing members are repositionable with respect to each other.

6. The dynamic stabilization system according to claim 1, wherein said stabilizing member is effective to limit the range of motion of an injured spine to approximately 80% of the initial uninjured spine.

7. The dynamic stabilization system according to claim 1, wherein said stabilizing member includes first and second mounting elements positioned at opposite ends thereof.

8. The dynamic stabilization system according to claim 7, wherein said first and second mounting elements are ball joints.

9. The dynamic stabilization system according to claim 8, wherein said ball joints are mounted with respect to said first and second pedicle screws.

10. The dynamic stabilization system according to claim 1, wherein said stabilizing member delivers stabilizing forces to a corresponding pair of pedicles of a spine by way of the first and second pedicle screws that have a limited impact on the location of the center of rotation for the pedicles of the corresponding pair.

11. The dynamic stabilization system according to claim 1, wherein said first and second springs define nested coil springs.

12. A method for stabilizing a spinal segment, comprising:
positioning a spinal stabilization device between first and second pedicle screws that are mounted with respect to a first and a second pedicle of the spinal segment, said spinal stabilization device including a first spring and a second spring that together deliver a force of between about 150 lbs/inch and 450 lbs/inch with respect to the first and second pedicle screws, and restrict the relative travel distance between the first and second pedicle screws to a distance of between about 1.5 mm and 5 mm.

13. The method according to claim 12, wherein said spinal stabilization device further includes first and second ends that are adapted to cooperate with pedicle mounting structures.

14. The method according to claim 13, wherein at least one of said pedicle mounting structures is a ball joint.

15. The method according to claim 12, wherein said first and second springs are subject to a preload.

16. The method according to claim 12, wherein said first and second springs define nested coil springs.

* * * * *

UNITED STATES PATENT AND TRADEMARK OFFICE
CERTIFICATE OF CORRECTION

| | | |
|---|---|---|
| PATENT NO. | : 7,713,287 B2 | |
| APPLICATION NO. | : 11/132538 | |
| DATED | : May 11, 2010 | |
| INVENTOR(S) | : Jens Peter Timm and Manohar M. Panjabi | |

It is certified that error appears in the above-identified patent and that said Letters Patent is hereby corrected as shown below:

In the specification:

Insert at col. 1, line 3 -- STATEMENT REGARDING FEDERALLY SPONSORED RESEARCH

This invention was made with government support under Grant No. AR045452 awarded by the National Institute of Health. The government has certain rights in the invention. --

Signed and Sealed this
Twentieth Day of December, 2011

David J. Kappos
*Director of the United States Patent and Trademark Office*